United States Patent
Tsujino et al.

(10) Patent No.: US 7,135,184 B2
(45) Date of Patent: Nov. 14, 2006

(54) CULTURE HAVING PHENOL OXIDASE-LIKE ACTIVITY

(75) Inventors: Yoshio Tsujino, Kobe (JP); Katsunori Endo, Kobe (JP); Abul Khaer Mohamad Quamrul Hasan, Kobe (JP)

(73) Assignee: Mandom Corporation, Osaka (JP)

( * ) Notice: Subject to any disclaimer, the term of this patent is extended or adjusted under 35 U.S.C. 154(b) by 60 days.

(21) Appl. No.: 10/515,968

(22) PCT Filed: Aug. 28, 2003

(86) PCT No.: PCT/JP03/10897

§ 371 (c)(1),
(2), (4) Date: Nov. 29, 2004

(87) PCT Pub. No.: WO2004/020617

PCT Pub. Date: Mar. 11, 2004

(65) Prior Publication Data

US 2005/0170485 A1    Aug. 4, 2005

(30) Foreign Application Priority Data

Aug. 29, 2002   (JP)   .............................. 2002-251910

(51) Int. Cl.
*A01N 65/00*    (2006.01)
*C12N 9/06*     (2006.01)
*D06P 5/00*     (2006.01)

(52) U.S. Cl. .................. 424/195.15; 8/400; 435/191

(58) Field of Classification Search ........... 424/195.15; 435/191; 8/400
See application file for complete search history.

(56) References Cited

FOREIGN PATENT DOCUMENTS

| | | |
|---|---|---|
| JP | 55-021755 A | 2/1980 |
| JP | 60-156385 A | 8/1985 |
| JP | 60-156385 A | 8/1985 |
| JP | 61-040786 A | 2/1986 |
| JP | 10-501137 A | 2/1998 |
| JP | 10-501137 A | 2/1998 |
| JP | 10-262690 A | 10/1998 |
| JP | 10-262690 A | 10/1998 |
| JP | 2001-073280 A | 3/2001 |
| JP | 2001-514513 A | 9/2001 |
| JP | 2001-514513 A | 9/2001 |
| WO | WO-95/01426 A1 | 1/1995 |
| WO | WO 95/33836 A1 | 12/1995 |
| WO | WO-97/28257 A1 | 8/1997 |
| WO | WO 98/40471 A1 | 9/1998 |

OTHER PUBLICATIONS

Materials on Workshop for High-Technology; 2001, University of Fukui, Center for Cooperative Research in Science and Technology, p. 55-57.
J. S. Lee et al.; Korean Journal of Mycology, vol. 13, No. 2, pp. 111-114, 1985.
Lee, J.S. et al., "Production and enzymatic properties of laccase from flammulina-velutipes", Korean Journal of Mycology, 1985, vol. 13, No. 2, pp. 111-114.
B.N. Naik et al.; Geobios, vol. 10, No. 5, 1983, pp. 218-222.
M. Pal et al.; World Journal of Microbiology and Biotechnology, Rapid Communications of Oxford, vol. 11, No. 5, Sep. 1995, pp. 541-545.
U. Kues et al.; Applied Microbiology and Biotechnology, vol. 54, No. 2, Aug. 2000, pp. 141-152.

Primary Examiner—Herbert J Lilling
(74) Attorney, Agent, or Firm—Birch, Stewart, Kolasch, and Birch, LLP

(57) ABSTRACT

It is intended to provide means of efficiently, economically and conveniently dyeing fibers or hair, bleaching pulp or fibers, removing phenol compounds from liquid wastes, degrading endocrine disruptors, producing phenolic resins, producing artificial lacquer coatings, improving wood qualities, etc. A culture of a strain belonging to the genus *Flammulina*; a culture originating in the above strain which is obtained by culturing the strain at a pH value exceeding 7 and has a phenol oxidase-like activity; a process for producing the culture; a dyeing method which comprises contacting a subject to be dyed with a dye in the presence of the above culture; and a dyeing composition containing the above culture.

9 Claims, 10 Drawing Sheets

A

B

C

D

CULTURE HAVING PHENOL OXIDASE-LIKE ACTIVITY

TECHNICAL FIELD

The present invention relates to a culture having phenol oxidase-like activity and a method for producing the culture, a staining method and a staining composition. More specifically, the present invention relates to a culture useful in staining of fiber and hair, bleaching of pulp and fiber, removal of a phenolic compound or the like in waste liquor, degradation of endocrine disruptors, preparation of a phenolic resin, production of artificial lacquer, improvement in woody properties and the like, a production method, capable of obtaining the culture conveniently and inexpensively in a large amount, a method for staining fibers, hair or the like, capable of staining with various dyes, and a staining composition useful for such staining.

BACKGROUND ART

Oxidases showing oxidization actions on various substrates such as phenolic compounds and polyphenolic compounds can be mainly classified into two groups of peroxidases and phenol oxidases.

The above-mentioned peroxidases catalyze oxidation of various substrates and require the presence of hydrogen peroxide as a common substrate in a reaction system. On the other hand, the phenol oxidases catalyze oxidation of various substrates and require the presence of molecular oxygen as a common substrate. Therefore, among known oxidases, since the above-mentioned phenol oxidases can catalyze oxidation of various substrates in the presence of oxygen in the air, the phenol oxidases are suitable for diversified chemical reactions such as coloring, decolorization, polymerization and degradation caused by generation of radical species as intermediates in the presence of oxygen.

The above-mentioned phenol oxidases have various catalytic abilities based on the action of radical species formed as reaction intermediates. For instance, it has been disclosed that when phenothiazine-10-propionic acid is used as a mediator, the degradation reaction of indigo can be efficiently carried out with laccase, which is a phenol oxidase (2001, University of Fukui, Center for Cooperative Research in Science and Technology, "Materials on Workshop for High-Technology," p. 55).

The above-mentioned oxidases have conventional been found in various plants, bacteria, fungi and the like. For instance, in the plants, the above-mentioned oxidases have been found in secretory pipe of *Anacardiaceae*, peaches, chestnuts, and those belonging to *Podocarpaceae*. In the fungi, the above-mentioned oxidases have been found in *Aspergillus, Botrytis, Myrothecium, Penicillium, Pestalotia, Rhizoctonia* and the like belonging to the genus *Deuteromycotina; Pleurotus, Lentinus, Polyporus, Trametes, Coriolus* and the like belonging to the genus *Basidiomycotina; Podospora, Neurospora, Monocillium* and the like belonging to the genus *Ascomycotina*. In the bacteria, the above-mentioned oxidases have been found in *Bacillus, Azospirillum, Streptomyces, Aerobacter* and the like. In addition, in the edible mushrooms, which are Basidimysetes, the above-mentioned oxidases have been found in, for instance, *Schizophyllum commune, Coriolus versicolor, Pycnoporus coccineus, Pleurotus octreatus, Fomitella fraxinea* and the like.

However, since many phenol oxidases possess the optimum pH near an acidic pH due to their limited uses. In addition, phenol oxidases having the optimum pH in the neutral to alkaline pH may not efficiently act on various substrates near the neutral pH because their optimum pHs are greatly changed depending upon the substrates used.

On the other hand, *Flammulina velutipes* has been found to exhibit laccase activity by culturing *Flammulina velutipes* in a medium at a pH of 6.0 (Japanese Patent Laid-Open No. Sho 60-156385).

However, the above-mentioned laccase is an enzyme having the optimum pH on the acidic pH, and has a defect that the activity is lowered in a pH of the neutral to alkaline region.

DISCLOSURE OF INVENTION

An object of the present invention is to provide a culture of a strain belonging to the genus *Flammulina*, which can be used in reaction of various compounds, particularly phenolic compounds, aminophenolic compounds and diaminophenolic compounds as substrates, and is excellent in applicability to efficient staining of fiber and hair, bleaching of pulp and fiber, removal of a phenolic compound in waste liquor, degradation of endocrine disruptors, preparation of phenolic resin, production of artificial lacquer, and improvement in woody properties. Also, an object of the present invention is to provide a method of producing the culture, capable of obtaining the above-mentioned culture easily and inexpensively in a large amount. Further, an object of the present invention is to provide a staining method, capable of staining efficiently and easily with various dyes, specifically phenolic compounds, aminophenolic compounds, diaminophenolic compounds, naturally occurring materials (flavonoids and the like), black-pigment constituents in animals and plants, and the like. In addition, an object of the present invention is to provide a staining composition which is easily handled and is capable of staining with various dyes, specifically phenolic compounds, aminophenolic compounds, diaminophenolic compounds, naturally occurring materials (flavonoids and the like), black-pigment constituents in animals and plants, and the like.

The summary of the present invention is:

[1] a culture from a strain belonging to the genus *Flammulina*, wherein the culture has phenol oxidase-like activity and at least one substrate specificity selected from the group consisting of ① to ⑩:

① catalyzing an oxidative decolorization reaction [decolorization activity] of each of:

Evans' Blue represented by the formula (I):

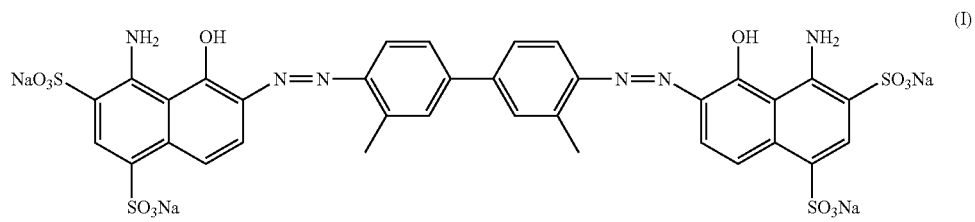

Acid Blue 80 represented by the formula (II):

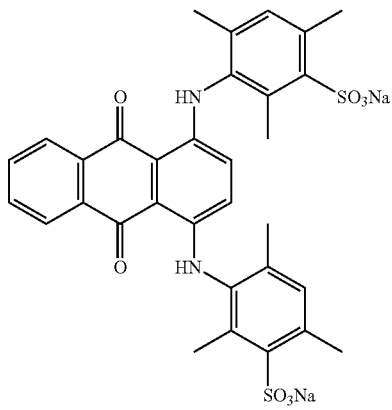

Remazol Brilliant Blue R represented by the formula (III):

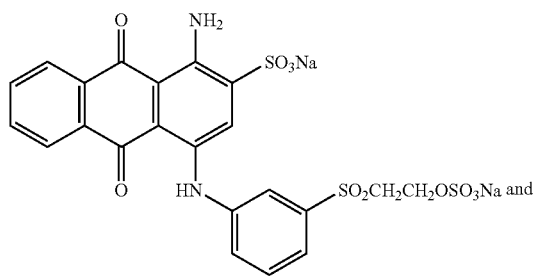

Acid Violet 17 represented by the formula (IV):

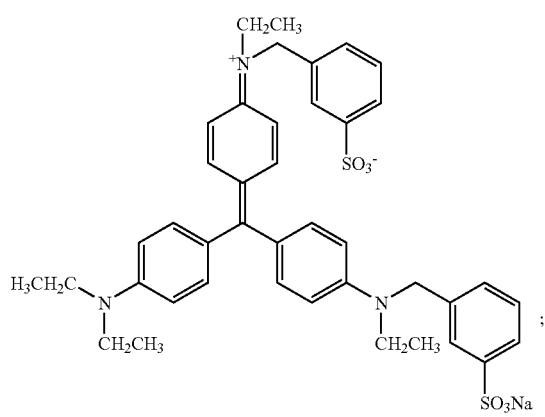

② catalyzing oxidative degradation reaction [oxidative degradation activity] for lignin;

③ catalyzing oxidative polymerization reaction [oxidative polymerization activity] of Indigo Carmine represented by the formula (V):

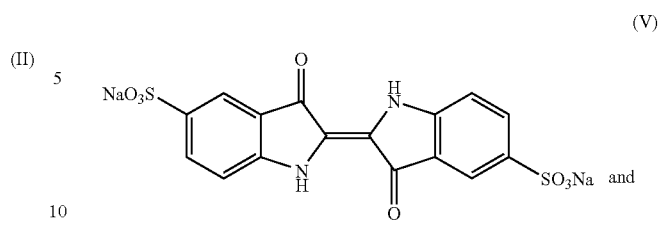

Natural Orange 6 represented by the formula (VI):

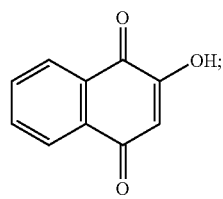

④ catalyzing oxidative coupling reaction [oxidative coupling activity] of 4-aminoantipyrine with one kind of a compound selected from the group consisting of phenolic compounds, aminophenolic compounds, diaminophenolic compound and heterocyclic compounds; and ⑤ catalyzing direct oxidative reaction [direct oxidation activity] of one kind of a compound selected from the group consisting of phenolic compounds, aminophenolic compounds, diaminophenolic compounds and heterocyclic compounds;

[2] the culture according to the above [1], wherein the strain belonging to the genus *Flammulina* is *Flammulina velutipes*;

[3] the culture according to the above [2], wherein *Flammulina velutipes* is *Flammulina velutipes* strain IFO 30601;

[4] the culture according to any one of claims 1 to 3, wherein the culture is obtainable by culturing a strain belonging to the genus *Flammulina* under pH conditions exceeding a pH of 7, and removing hyphae from the resulting culture medium;

[5] a culture from a strain belonging to the genus *Flammulina*, wherein the culture is obtainable by culturing a strain belonging to the genus *Flammulina* under pH conditions exceeding a pH of 7, and removing hyphae from the resulting culture medium, wherein the culture has phenol oxidase-like activity;

[6] a method for producing the culture from a strain belonging to the genus *Flammulina* according to any one of the above [1] to [5], characterized in that the method comprises culturing a strain belonging to the genus *Flammulina*, and removing hyphae from the resulting culture medium, to give a culture;

[7] the method according to the above [6], wherein the strain belonging to the genus *Flammulina* is *Flammulina velutipes*;

[8] the method according to the above [7], wherein *Flammulina velutipes* is *Flammulina velutipes* IFO 30601 strain;

[9] a staining method characterized in that the staining method comprises contacting a subject to be stained with a dye in the presence of the culture of any one of the above [1] to [5]; and

[10] a staining composition comprising the culture of any one of the above [1] to [5].

BRIEF DESCRIPTION OF THE DRAWINGS

In FIG. 5, panel A shows the results using the yak hair bundle, and panel B shows the results using the wool cloth.

BEST MODE FOR CARRYING OUT THE INVENTION

Figure 1:
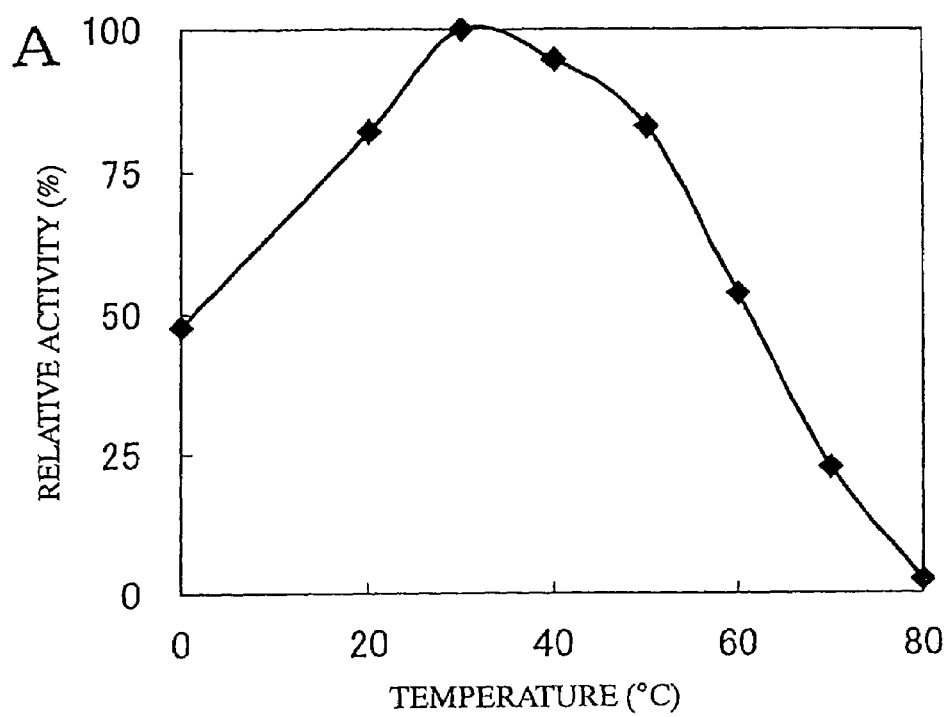
FIG. 1 is a diagram showing the results for examining the optimum temperature of the culture of the present invention. Panel A of the figure shows the case where 2,6-dimethoxyphenol was used as a substrate, and panel B shows the case where o-aminophenol was used as a substrate.
Figure 1:
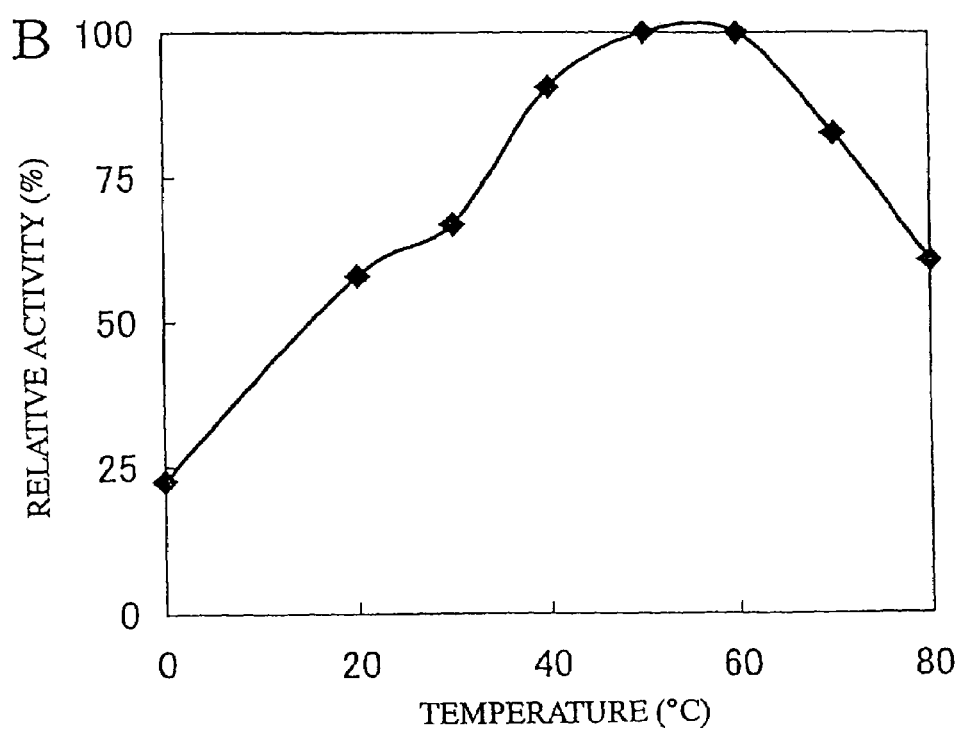

The culture of the present invention has phenol oxidase-like activity, and can thus catalyze various chemical reactions resulting from generation of radical species as reaction intermediates in the presence of oxygen. In addition, the culture of the present invention possesses a high activity in the neutral range, with the optimum pH hardly changing depending on the substrate used. Accordingly, the culture of the present invention exhibits excellent effects such as staining of fiber and hair, bleaching of pulp and fiber, removal of phenolic compounds from waste liquor, degradation of endocrine disruptors, production of phenolic resin, production of artificial lacquer, production of an adhesive and the like. Since the culture of the present invention is derived from a strain belonging to the genus *Flammulina* represented by edible *Flammulina velutipes* described later, the culture of the present invention exhibits an excellent effect that the culture can be easily supplied from culture products released outside of hyphae.

The strain belonging to the genus *Flammulina* includes, specifically *Flammulina velutipes*, more specifically *Flammulina velutipes* strain IFO30601.

In the present specification, the phenol oxidase-like activity refers to an activity of catalytically oxidizing a phenolic compound, an aminophenolic compound, a phenylenediamine compound and the like in the presence of oxygen. Such phenol oxidase-like activity can be measured, for example, by a coloring reaction due to a reaction of reducing an oxygen molecule with a phenol, aniline derivative, or the like as a hydrogen donor. The hydrogen donor includes a phenolic compound, an aminophenolic compound, a diaminophenolic compound, a heterocyclic compound, and the like.

The culture of the present invention has at least one substrate specificity selected from the group consisting of:

① catalyzing oxidative decolorization reactions [decolorization activity] of:

Evans' Blue represented by the formula (I):

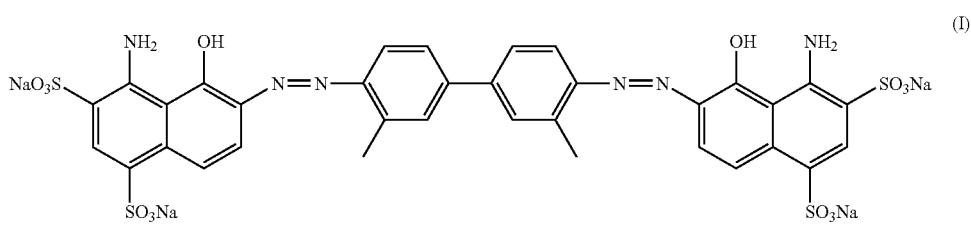

Acid Blue 80 represented by the formula (II):

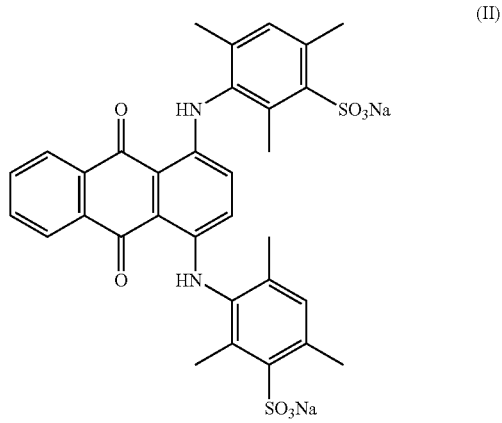

Remazol Brilliant Blue R represented by the formula (III):

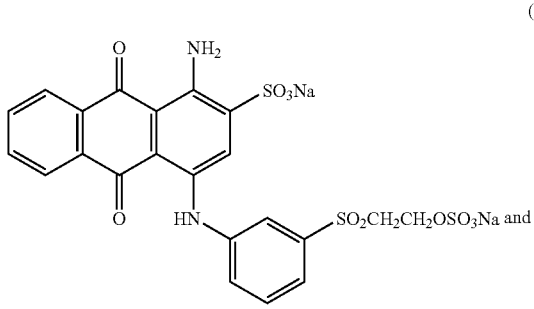

Acid Violet 17 represented by the formula (IV):

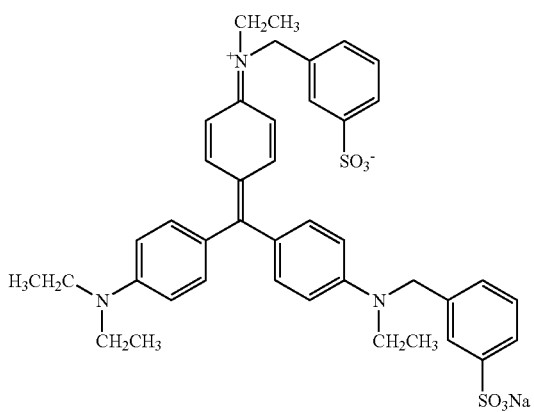

② catalyzing oxidative degradation reaction [oxidative degradation activity] of lignin,
③ catalyzing oxidative polymerization reaction [oxidative polymerization activity] of Indigo Carmine represented by the formula (V):

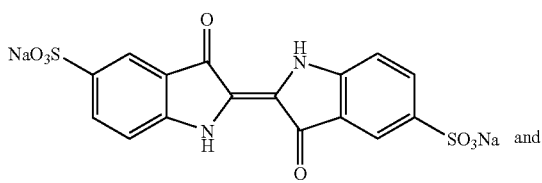

Natural Orange 6 represented by the formula (VI):

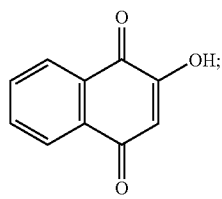

④ catalyzing oxidative coupling reaction [oxidative coupling activity] of 4-aminoantipyrine with one kind of a compound selected from the group consisting of a phenolic compound, an aminophenolic compound, a diaminophenolic compound and a heterocyclic compound, and
⑤ catalyzing direct oxidative reaction [direct oxidation activity] of one kind of a compound selected from the group consisting of a phenolic compound, an aminophenolic compound, a diaminophenolic compound and a heterocyclic compound.

The phenolic compound includes, for example, phenol, 2-methoxyphenol, 2,6-dimethoxyphenol, catechol, resorcinol, hydroquinone, pyrogallol, gallic acid, propyl gallate, 1-naphthol, catechin and the like. The aminophenolic compound includes, for example, o-aminophenol, m-aminophenol, p-aminophenol and the like. The diaminophenolic compound includes, for example, o-phenylenediamine, m-phenylenediamine, p-phenylenediamine and the like. The heterocyclic compound includes 5-hydroxyindole, 2,6-diaminopyridine and the like.

Regarding the substrate specificity, the decolorization activity in the above item ①, the oxidative degradation activity of the above item ②, and the oxidative polymerization activity of the above item ③ were determined by:

a) a step of pre-incubating 950 µl of 105.3 mM sodium phosphate buffer (pH 7.0) containing a substrate (dye, lignin or the like) at 25° C. for 5 minutes, to give a substrate solution,
b) a step of mixing the substrate solution obtained in the step a) with 50 µl of a culture solution containing the culture of the present invention and then incubating the resulting mixture at 25° C. for 60 minutes, and
c) a step of measuring the absorbance of the product obtained in the step b), at a wavelength depending on the substrate. The decolorization activity on the respective dyes can be evaluated by measuring as the dye, Evans' Blue, Acid Blue 80, Remazol Brilliant Blue R and Acid Violet 17 in the step c) for their absorbance at 600 nm, 600 nm, 600 nm and 550 nm respectively. In addition, regarding the lignin, the oxidative degradation activity on the respective dyes can be evaluated by measuring the absorbance at 450 nm in the step c). The oxidative polymerization activity on the respective dyes can be evaluated by measuring as the dye, Indigo Carmine and Natural Orange 6 in the step c) for their absorbance at 600 nm and 450 nm respectively.

The oxidative coupling activity in the above item ④ is determined by:

a) a step of pre-incubating 190 µl of 105.3 mM phosphate buffer (pH 7.0) containing 0.4 µmol hydrogen donor and 4.0 µmol 4-aminoantipyrine at 25° C. for 1 minute, to give a substrate solution,
b) a step of mixing the substrate solution obtained in the step a) with 10 µl of a culture solution containing the culture of the present invention, and then incubating the mixture at 25° C. for 60 minutes, and
c) a step of measuring the absorbance of the product obtained in the step b), at a wavelength depending on the hydrogen donor, wherein a change in absorbance at 490 nm is measured when a phenolic compound, a diaminophenolic compound or a heterocyclic compound is used as the substrate, or a change in absorbance at 450 nm is measured when an aminophenolic compound is used as the substrate.

The direct oxidation activity in the above item ⑤ is determined by:

a) a step of pre-incubating 180 µl of 0.89 mM sodium phosphate buffer (pH 7.0) containing 0.1 mmol substrate at 25° C. for 1 minute, to give a substrate solution, b) a step of mixing the substrate solution obtained in the step a) with 20 µl of a culture solution containing the culture of the present invention and then incubating the mixture at 25° C. for 60 minutes, and c) a step of measuring a change in the absorbance of the product obtained in the step b), at 490 nm, 450 nm or 405 nm depending on the substrate.

The culture of the present invention exhibits an excellent phenol oxidase-like activity in a pH range of from 6.0 to 8.0. Since the culture of the present invention exhibits an excellent phenol oxidase-like activity on various phenolic compounds in the pH range described above, the culture exhibits an excellent property that it can effect efficient reaction without particular pH adjustment.

The culture of the present invention exhibits an excellent phenol oxidase-like activity in the range of 20° to 60° C. Since the culture of the present invention exhibits an excellent phenol oxidase-like activity in the above temperature range, the culture exhibits a high activity in the living temperature (room temperature, water temperature, body temperature, ambient temperature or the like) without regulating the conditions at specific temperature. Accordingly, staining, disposal of waste liquor, synthesis of polymer, and the like can be easily carried out.

When the culture of the present invention is incubated at 30° C. for 1 hour in a pH range of from 5.0 to 9.5, the culture of the present invention maintains a relative remaining activity of about 75% or more as compared to the activity before incubation. In addition, when the culture of the present invention is incubated at 30° C. for 1 hour in a pH range of from 4.0 to 10.5, the culture of the present invention maintains a relative remaining activity of about 40% or more as compared to the activity before incubation. Regarding the pH stability of the phenol oxidase compound in the present invention, when the culture of the present invention is incubated at 30° C. for 20 hours, the culture maintains a relative remaining activity of about 75% or more in a pH range of from 7.0 to 9.0, as compared to the activity before incubation. Since the culture of the present invention exhibits excellent pH stability in the above pH range, the culture of the present invention exhibits an excellent property that a water-based reaction solution can be used without adjusting the conditions at specific pH.

In addition, when the culture of the present invention is incubated at a pH of 6.0 for 1 hour at 0° to 40° C., the culture of the present invention maintains a relative remaining activity of about 75% or more as compared to the activity before incubation. Since the culture of the present invention exhibits excellent thermal stability in the above temperature range, the culture of the present invention exhibits an excellent property that it can be used and stored at ambient temperatures without regulating the conditions at specific temperature. Accordingly, there can be exhibited an excellent effect that staining, disposal of waste liquor, synthesis of polymer, and the like can be carried out inexpensively and easily.

One of significant features of the culture of the present invention is also resides in that the culture is a culture obtained by culturing a strain belonging to the genus *Flammulina* under pH conditions exceeding a pH of 7, and then removing hyphae from the resulting culture solution.

The culture of the present invention is obtained by culturing a strain belonging to the genus *Flammulina* under pH conditions exceeding a pH of 7, and exhibits an excellent property that it shows a stable and high phenol oxidase-like activity in a pH range of from 6.0 to 8.0.

In the present specification, the "pH conditions exceeding a pH of 7" refer to conditions having a pH value higher than a pH exceeding a pH of 7 and lower than a pH of 13.0, preferably a pH value of pHs of from 7.5 to 11.0, more preferably a pH value of pHs of from 8.0 to 10.0.

The culture of the present invention may be a culture solution obtained by culturing a strain belonging to the genus *Flammulina*, or may be a product obtained by removing hyphae from the culture solution. Therefore, the culture of the present invention can be provided easily from a culture product outside of hyphae, obtained by culturing a strain belonging to the genus *Flammulina* in a suitable medium. Since the removed hyphae can be cultured in a new medium to give the culture of the present invention, the hyphae can be recycled. The present invention encompasses a method for producing the culture of the present invention.

One of the significant features of the production method of the present invention resides in that the culture is obtained by culturing a strain belonging to the genus *Flammulina* and then removing hyphae from the resulting culture medium.

According to the production method of the present invention, there can be brought about an excellent effect that a culture having phenol oxidase-like activity can be obtained easily in a large amount by culturing a strain belonging to the genus *Flammulina*. Further, since the culture of the present invention can be obtained by culturing the removed hyphae in a new medium to give the culture of the present invention, the removed hyphae can be recycled. Therefore, there is exhibited an excellent effect that the culture of the present invention can be obtained inexpensively and easily.

For culturing the strain belonging to the genus *Flammulina*, a liquid or solid medium may be used.

The carbon source in the culture used in the production method of the present invention includes, as long as the carbon source may be a source which may be metabolized by the strain belonging to the genus *Flammulina*, sugar such as glucose, sucrose, molasses and starch; bran, mandarin orange pulp and the like. The carbon source can be used alone or as a mixture of two or more thereof. The nitrogen source includes an organic nitrogen source such as soybean fiber, peptone, trypton, casamino acid, yeast extract, malt extract, defatted soybean powder, corn steep liquor and urea; and an inorganic nitrogen source such as potassium nitrate and ammonium sulfate. The nitrogen source can be used alone or as a mixture of two or more thereof. The medium used in the production method of the present invention may be supplemented if necessary with inorganic salts such as phosphates, magnesium sulfate, magnesium carbonate, sodium carbonate, potassium, calcium, iron, copper, zinc, manganese and cobalt, vitamins and the like. The concentration of the carbon source, nitrogen source and the like in the medium may be a concentration at which basidiomycetes producing the culture of the present invention, particularly a strain belonging to the genus *Flammulina*, can grow sufficiently to exhibit phenol oxidase-like activity, and specifically the carbon source is desired to be 0.1 to 20% by weight, preferably 1 to 10% by weight, and the nitrogen source is desired to be 0.1 to 10% by weight, preferably 1 to 5% by weight.

The pH of the medium may be a pH at which a strain belonging to the genus *Flammulina* can grow sufficiently to exhibit phenol oxidase-like activity, particularly phenol oxidase-like activity with the substrate specificity, further phenol oxidase-like activity showing the above reaction optimum pH, and from the viewpoint of sufficiently exhibiting phenol oxidase-like activity with the above properties (for example, substrate specificity, reaction optimum pH and the like), the pH is preferably exceeding a pH of 7.0 (initial pH), preferably pHs of from 7.5 to 11.0, more preferably pHs of from 8.0 to 10.0. Accordingly, the medium is used desirably after adjustment to such pH and subsequent sterilization.

The culture temperature may be a temperature at which filamentous fungi can grow, and is practically 10° to 40° C., preferably 20° to 35° C.

When the strain belonging to the genus *Flammulina* is cultured in a liquid medium, aeration culture or shake culture is desired.

The culture time is varied depending on various culture conditions, and in the case of aeration culture, it is desired that the culture time is 2 to 10 days. The culture time can be set so as to allow the culture medium to attain a highest activity.

The culture of the present invention is produced in secretion outside of the cell and accumulated in the culture solution. Accordingly, the culture solution can be used as it is, or can be obtained as a conditioned medium by removing unnecessary materials such as the microorganism by centrifugation or filtration through a filter paper or a filter cloth after culture.

In the present invention, the phenol oxidase-like activity of the culture obtained as a culture solution or as a conditioned medium can further be increased or subjected to decolorization, concentration, freeze drying, dialysis, salting-out or the like from the viewpoint of blending it into products such as cosmetics, and non-pharmaceutical preparations.

In addition, according to the culture of the present invention, staining of keratin fibers can be carried out by using the culture together with various dyes, colorants and the like. Accordingly, the present invention provides a staining method.

One of the significant features of the staining method of the present invention resides in that a subject of staining is brought into contact with a dye in the presence of the culture. According to the staining method of the present invention, since the culture of the present invention is used, a subject of staining can be stained inexpensively and easily with various dyes. In addition, according to the staining method of the present invention, since the culture of the present invention is used, the method can be carried out under external environmental conditions without regulating conditions at special temperature or pH.

The subject of staining includes, for example, cotton, diacetate, flax, linen, liocel, polyacryl, polyamide, polyester, ramie, laen, tencel, triacetate, fur, animal skin, hide, silk or wool clothes, yarn, fiber, clothing, wood, hair, film and the like.

The dyes such as indoline and indoline compounds, indole compounds and oxidized dyes described in standards of materials of non-pharmaceutical preparations can be oxidized as substrates, and a coupling agent can also be used.

Concretely, the indoline and the indoline compounds can be exemplified by indoline, 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 4-methoxy-6-hydroxyindoline, N-hexyl-5,6-dihydroxyindoline, 2-methyl-5,6-dihydroxyindoline, 3-methyl-5,6-dihydroxyindoline, 4-hydroxyindoline, 2,3-dimethyl-5,6-dihydroxyindoline, 2-methyl-5-ethyl-6-hydroxyindoline, 2-methyl-5-hydroxy-6-β-hydroxyethylindoline, 4-hydroxypropylindoline, 2-hydroxy-3-methoxyindoline, 6-hydroxy-5-methoxyindoline, 6-hydroxyindoline, 5-hydroxyindoline, 7-hydroxyindoline, 7-aminoindoline, 5-aminoindoline, 4-aminoindoline, 5,6-dihydroxyindolinecarboxylic acid, 1-methyl-5,6-dihydroxyindoline, and salts thereof, and the like.

Concretely, the indole compound includes 4-hydroxyindole, 5-hydroxyindole, 5,6-dihydroxyindole, 5,6-dihydroxyindole-2-carboxylic acid, 5,6-tri(t-butoxycarbonyloxy)indole, 5,6-di(t-butoxycarbonyloxy)indole, 5-t-butoxycarbonyloxy-6-hydroxyindole, 6-t-butoxycarbonyloxy-5-hydroxyindole, 5,6-di(ethoxycarbonyloxy)indole, 5,6-di(ethylcarbamoyloxy)indole, 1-pivaloyl-5-(pivaloyloxymethoxy)-6-pivaloyloxyindole, 1-pivaloyl-5-pivaloyloxymethoxy-6-hydroxyindole, 5,6-(oxycarbonylmethoxy)indole, and the like.

Concretely, the oxidative dyes listed under the provision of raw materials of quasi-drugs can be exemplified by 5-amino-o-cresol, o-aminophenol, m-aminophenol, p-aminophenol, 2,6-diaminopyridine, 5-(2-hydroxyethylamino)-2-methylphenol, N,N-bis(β-hydroxy)-p-phenylenediamine sulfate, p-nitro-o-phenylenediamine, sodium p-nitro-2',4'-diaminoazobenzene sulfate, toluene-2,5-diamine, 5-amino-o-cresol sulfate, p-aminophenol sulfate, o-chloro-p-phenylenediamine sulfate, 4,4'-diaminodiphenylamine sulfate, p-methylaminophenol sulfate, p-phenylenediamine sulfate, m-phenylenediamine sulfate, toluene-2,5-diamine sulfate, 2,4-diaminophenoxyethanol hydrochloride, toluene-2,5-diamine hydrochloride, m-phenylenediamine hydrochloride, 2,4-diaminophenol hydrochloride, 3,3'-iminodiphenol, p-phenylenediamine hydrochloride, N-phenyl-p-phenylenediamine hydrochloride, N-phenyl-p-phenylenediamine acetate, 1,5-dihydroxynaphthalene, toluene-3,4-diamine, p-methylaminophenol, N,N'-bis(4-aminophenyl)-2,5-diamino-1,4-quinonediimine, o-aminophenol sulfate, 2,4-diaminophenol sulfate, m-aminophenol sulfate, and the like.

In addition, in the present invention, there can be also used direct dyes such as 2-amino-4-nitrophenol, 2-amino-5-nitrophenol, 1-amino-4-methylaminoanthraquinone, nitro-p-phenylenediamine hydrochloride, 1,4-diaminoanthraquinone, nitro-p-phenylenediamine, picramic acid, sodium picramate, 2-amino-5-nitrophenol sulfate, resorcinol, nitro-p-phenylenediamine sulfate, p-nitro-o-phenylenediamine sulfate, p-nitro-m-phenylenediamine sulfate, and the like.

The contact of a subject of staining with a dye in the presence of the culture can be carried out, for example, by mixing the dye with the culture just before use and then contacting the mixture with the subject of staining, or by contacting a mixture of the dye and the culture stored under anaerobic conditions, with the subject of staining in the air.

The culture of the present invention provides a staining composition.

One of significant features of the staining composition of the present invention resides in that the staining composition comprises the culture of the present invention. Therefore, according to the staining composition of the present invention, there is exhibited an excellent effect that staining can be achieved efficiently with various dyes, particularly phenolic compounds, aminophenolic compounds, and phenylenediamine compounds, in the neutral pH range without significant change in the optimum pH in the presence of oxygen and under external environmental conditions.

From the viewpoint of practical staining time, the content of the culture of the present invention in the staining composition of the present invention is 0.05 to 100 KU, desirably 0.5 to 25 KU, as phenol oxidase-like activity, per 100 g of the hair staining composition. One unit (U) of phenol oxidase-like activity is defined as an amount for increasing absorbance at 490 nm by 1 per minute with 30 mM p-phenylenediamine as substrate under the conditions of 25° C. and pH 7.0.

In the staining composition of the present invention, there can be used dyes or colorants, specifically the above-mentioned indoline and indoline compounds, indole compounds, and oxidative dyes described in standards of materials of non-pharmaceutical preparations and the like can be used. A coupling agent can also be used. The direct dyes can also be used.

From the viewpoint of practical staining time, it is desired that the content of the dye or colorant in the staining composition of the present invention is 0.0005 to 12% by weight, preferably 0.005 to 6% by weight, in the staining composition.

The pH of the staining composition of the present invention may be adjusted with an acid, alkali or buffer suitable for allowing the culture of the present invention to exhibit its physiological activity, thereby achieving the staining. Concretely, there are included inorganic acids such as hydrochloric acid, sulfuric acid etc.; organic acids such as phosphoric acid, acetic acid, tartaric acid, citric acid, lactic acid, and sulfonic acid; ammonia; amines such as monoisopropanolamine, and monoethanolamine; carbonates such as ammonium and carbonate; and hydroxides such as sodium hydroxide, and potassium hydroxide.

In the staining composition, a reducing agent such as thiolactic acid, sodium sulfite, and N-acetyl-L-cysteine can be formulated thereto in such a range that the phenol oxidase-like activity is not inhibited. In addition to the above-described components, a surfactant, an oily component, silicone derivatives, a thickener, a solvent, water, a chelating agent, a perfume and the like can be suitably formulated in such a range that the effect of the present invention is not inhibited.

When the staining composition of the present invention is used as a hair staining composition, a staining composition of one-pack type comprising e.g. a dye and the culture is prepared under anaerobic conditions, and when used, the composition can be applied onto hair and contacted with the air, to stain the hair. Alternatively, a composition comprising the culture, and a composition comprising a dye can be mixed with each other as a staining composition of multi-pack type just before use and then applied onto hair, to stain the hair. The staining composition of the present invention can also be used in the form of various preparations suitable for staining, such as liquid, cream and gel.

Since the culture of the present invention has phenol oxidase-like activity, the culture is useful not only in staining fiber and hair but also in bleaching pulp and fiber, removing phenolic compounds in waste liquor, degrading endocrine disruptors, producing phenolic resin, producing artificial lacquer, and improving woody properties.

The present invention will be described hereinbelow more specifically by means of Examples, without intending to limit the present invention to these Examples.

EXAMPLE 1

Preparation of Culture of *Flammulina velutipes* (Strain IFO 30601)

(1) Preparation 1 of Culture

The following procedures were carried out in a clean bench.

*Flammulina velutipes* (strain IFO 30601) was sown to a sterilized petri dish containing 10 ml of a solid culture agar medium [composition: 2.4% by weight potato dextrose broth (manufactured by Difco), 2.0% by weight agar, and balance water] in an amount equivalent to a single loop of platinum, and cultured at 25° C. for 10 days. Thereafter, the hyphae grown on the whole agar medium were cut into small pieces of 5 mm each side with a sterilized loop of platinum.

Ten pieces of the above-mentioned small pieces were sown to a liquid culture medium 1 [composition: 2.4% by weight potato dextrose broth (manufactured by Difco), and balance water (pH 5.2); sterilized at 121° C. for 15 minutes], and culture with reciprocation shaking (150 reciprocations/min.) was carried out at 25° C. for 7 days.

The entire volume of the resulting culture medium was added to 500 ml of the above-mentioned liquid culture medium in a 2-L Erlenmeyer flask, and culture with reciprocation shaking (100 reciprocations/min.) was carried out at 25° C. for 3 weeks.

Thereafter, the grown pelletal hyphae were allowed to stand to be precipitated, to remove the culture medium. In addition, 500 ml of a liquid culture medium 2 [composition: 1.0% by weight glucose, 0.1% by weight yeast extract, 0.14% by weight $(NH_4)_2SO_4$, 0.36% by weight $K_2HPO_4$, 0.02% by weight $MgSO_4.7H_2O$, 0.1% mineral mixed solution (composition: 1.0% by weight $CuSO_4.5H_2O$, 1.0% by weight $ZnCl_2$, 0.7% by weight $FeCl_3.6H_2O$, 0.5% by weight $CoSO_4.7H_2O$, 0.5% by weight $MnCl_2.4H_2O$), pH 9.2; sterilized at 121° C. for 15 minutes] was added to the remaining hyphae, and culture was further carried out at 25° C. for 3 days.

Thereafter, the grown pelletal hyphae were allowed to stand to be precipitated. The culture was collected by decantation. The resulting culture was a pale yellow or yellowish brown, transparent or turbid liquid.

(2) Preparation 2 of Culture

The culture of *Flammulina velutipes* strain IFO 30601 obtained in the above (1) was filtered under reduced pressure, to give a filtrate.

The pH of the above-mentioned filtrate was adjusted to 7.5 with a 1 M aqueous sodium hydroxide. Five grams of DEAE-cellulose (manufactured by Sigma) carrier was added to 1 L of the obtained mixture, and stirred with shaking at 4° C. for 30 minutes. Thereafter, the mixture was allowed to stand for 10 minutes, and supernatant was removed.

To the DEAE-cellulose carrier obtained was added 0.1 M sodium phosphate buffer (pH 6.5) containing 1 M sodium chloride in an amount of 3 times the volume of the carrier. The mixture obtained was stirred with shaking for 5 minutes to elute a protein adsorbed to the DEAE-cellulose carrier. The eluent obtained was collected by filtration under reduced pressure and dialyzed against deionized water at 4° C. The resulting product was lyophilized, to give a culture as a lyophilized product.

EXAMPLE 2

Reaction Optimum Temperature of Culture of the Present Invention

One-hundred-and-two milligrams of the culture (lyophilized product) (amount of protein: 23 mg; specific activity: 15 U/mg protein) obtained in (2) in Example 1 mentioned above was dissolved so as to have a concentration of 0.02 mg protein/ml, to obtain a culture.

The phenol oxidase-like activity was assayed for the culture obtained under various temperature conditions (0°, 20°, 30°, 40°, 50°, 60°, 70° and 80° C.). Concretely, when o-aminophenol was used as a substrate, 0.89 ml of 100 mM sodium phosphate buffer (pH 6.0), 0.1 ml of a dimethyl sulfoxide solution of 50 mM o-aminophenol and 0.01 ml of the culture solution were mixed in a microcentrifuge tube (manufactured by Porex Bio Products Incorporated), and the reaction was carried out for the resulting mixture at each reaction temperature for 10 minutes. Thereafter, 0.1 ml of 2 M glycine-HCl buffer (pH 3.0) was added to the reaction mixture, whereby stopping the reaction. Alternatively, when 2,6-dimethoxyphenol was used as a substrate, the same procedures were carried out as the case of o-aminophenol solution mentioned above except that a 50 mM aqueous 2,6-dimethoxyphenol solution was used in place of o-aminophenol.

Next, the activity was evaluated for each of the resulting reaction products by determining absorbance at 420 nm in the case where o-aminophenol was used as a substrate, or determining absorbance at 470 nm in the case where 2,6-dimethoxyphenol was used as a substrate, with a spectrophotometer (manufactured by Jasco, trade name: V-530). Here, the above-mentioned activity by which absorbance was increased by 1 in one minute was defined as 1 U (unit). The results are shown in FIG. 1. In FIG. 1, the activity is expressed as a relative activity, the maximum activity of which is 100. In addition, panel A of the figure shows the case where 2,6-dimethoxyphenol was used as a substrate, and panel B shows the case where o-aminophenol was used as a substrate.

As shown in FIG. 1, it was seen that the reaction optimum temperature of the culture of the present invention is from 20° to 60° C.

EXAMPLE 3

Thermal Stability of Culture of the Present Invention

Pretreatment of 0.02 ml of the same culture solution as in Example 2 mentioned above was carried out under various temperature conditions (0°, 20°, 30°, 40°, 50°, 60°, 70° and 80° C.) by incubating the culture solution in 0.18 ml of 100 mM sodium phosphate buffer (pH 6.0) for 60 minutes.

Figure 2:
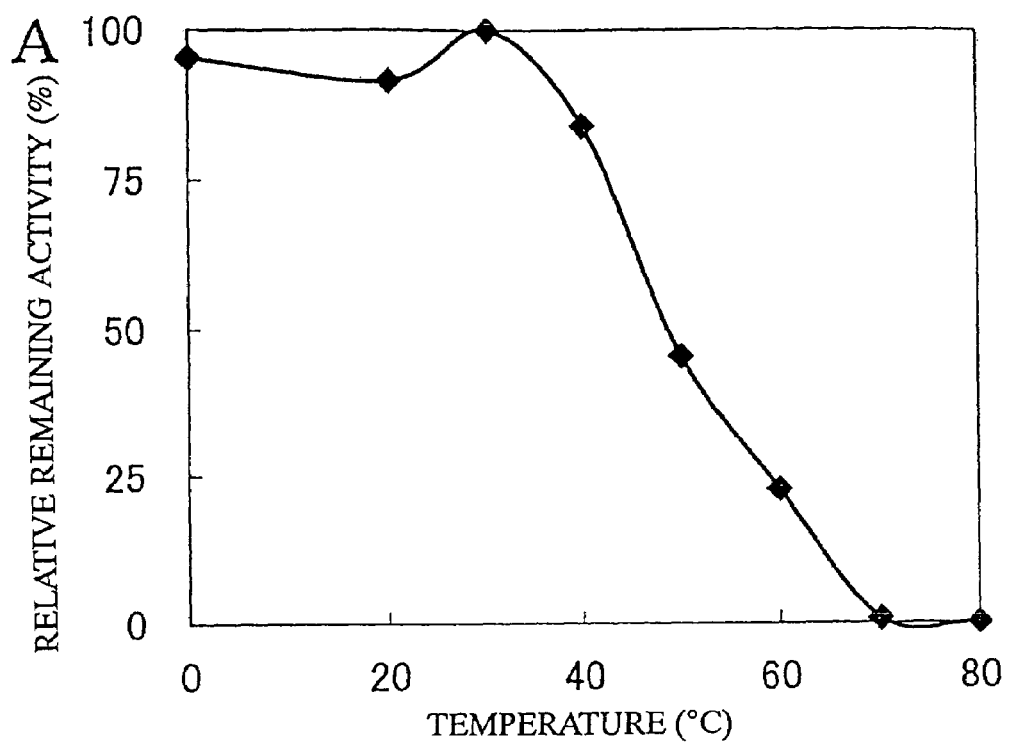
FIG. 2 is a diagram showing the results for examining the thermal stability of the culture of the present invention. Panel A of the figure shows the case where 2,6-dimethoxyphenol was used as a substrate, and panel B shows the case where o-aminophenol was used as a substrate.
Figure 2:
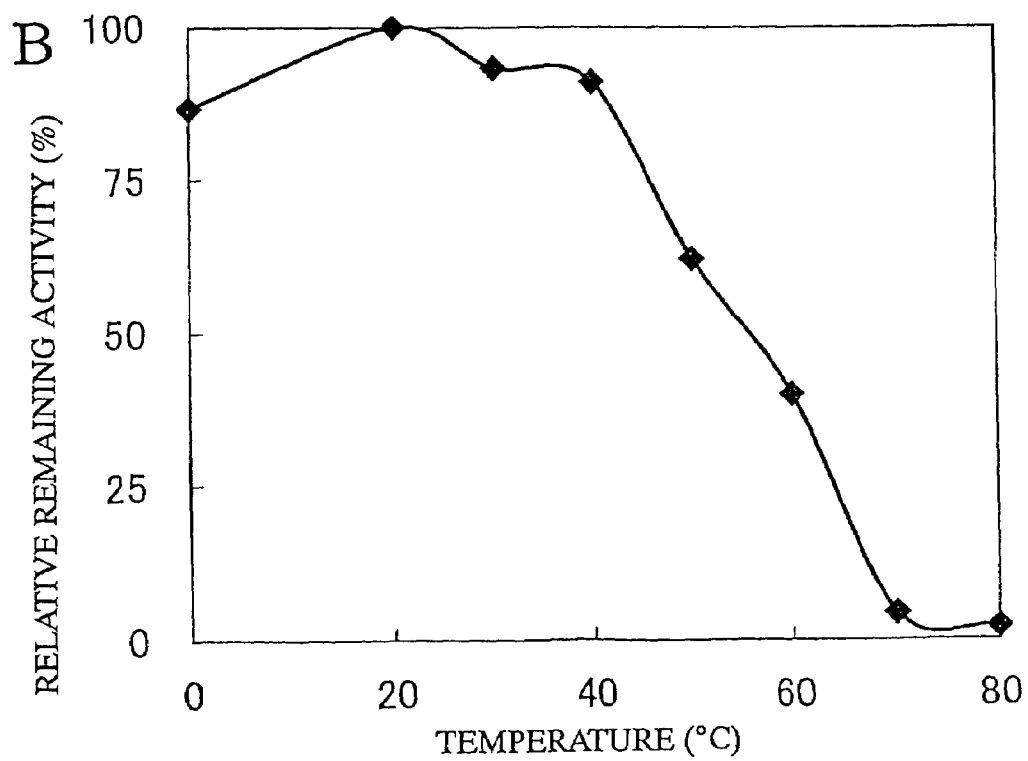

When o-aminophenol was used as a substrate, 0.05 ml of the resulting product, 0.85 ml of 100 mM sodium phosphate buffer (pH 6.0) and 0.1 ml of a dimethyl sulfoxide solution of 50 mM o-aminophenol were sufficiently mixed in a microcuvette. The activity was evaluated for the resulting mixture by determining a change in absorbance at 420 nm with a spectrophotometer (manufactured by Jasco, trade name: V-530). Alternatively, when 2,6-dimethoxyphenol was used as a substrate, the same procedures were carried out as in the above-mentioned case where o-aminophenol was used as a substrate by using 50 mM aqueous 2,6-dimethoxyphenol solution in place of 50 mM o-aminophenol in the dimethyl sulfoxide solution, and thereafter, the activity was evaluated by determining a change in absorbance at 470 nm. Here, 1 U (unit) of the activity was defined as an amount for increasing the absorbance by 1 per one minute. The results are shown in FIG. 2. In FIG. 2, the activity is expressed as a relative remaining activity, the maximum activity of which is 100. In addition, panel A of the figure shows the case where 2,6-dimethoxyphenol was used as a substrate, and panel B shows the case where o-aminophenol was used as a substrate.

As shown in FIG. 2, in the case of 2,6-dimethoxyphenol, the culture of the present invention showed a relative remaining activity of 84% at a temperature up to 40° C., a relative remaining activity of 45% at 50° C., and a relative remaining activity of 22% at 60° C. In the case of o-aminophenol, the culture of the present invention showed a relative remaining activity of 91% at a temperature up to 40° C., a relative remaining activity of 62% at 50° C., and a relative remaining activity of 40% at 60° C.

EXAMPLE 4

Optimum pH of Culture of the Present Invention

During the reaction of the culture of the present invention with each substrate, 0.2 M glycine-sodium hydroxide buffer (pH 11.5, pH 10.5, pH 9.5), 0.2 M Tris-HCl buffer (pH 10.0, pH 9.0, pH 8.0, pH 7.0), 0.2 M sodium phosphate buffer (pH 7.5, pH 7.0, pH 6.5, pH 6.0, pH 5.5), 0.2 M sodium acetate buffer (pH 5.5, pH 5.0, pH 4.5, pH 4.0, pH 3.5) and 0.2 M glycine-HCl buffer (pH 4.0, pH 3.5, pH 3.0, pH 2.0) were used as buffers depending upon the pHs.

When o-aminophenol was used as a substrate, 0.02 ml of the same culture solution as in Example 2 mentioned above, 0.88 ml of one of the above-mentioned various buffers, 0.1 ml of a dimethyl sulfoxide solution of 50 mM o-aminophenol were sufficiently mixed in a microcuvette. The activity was evaluated for the resulting mixture by determining a change in absorbance at 420 nm with a spectrophotometer (manufactured by Jasco, trade name: V-530). Alternatively, when 2,6-dimethoxyphenol was used as a substrate, the same procedures were carried out as in the above-mentioned case where o-aminophenol was used as a substrate by using 50 mM aqueous 2,6-dimethoxyphenol solution in place of the dimethyl sulfoxide solution of 50 mM o-aminophenol, and thereafter, the activity was evaluated by determining a change in absorbance at 470 nm.

When p-phenylenediamine was used as a substrate, 0.1 M Tris-HCl buffer (pH 9.0, pH 8.5, pH 8.0, pH 7.5, pH 7.0), 0.1 M sodium phosphate buffer (pH 9.0, 8.5, 8.0, pH 7.5, pH 7.0, pH 6.5, pH 6.0) and 0.1 M sodium citrate buffer (pH 8.0, pH 7.5, pH 7.0, pH 6.5, pH 6.0, pH 5.0, pH 4.0, pH 3.0) were used as buffers depending upon the pHs. The activity was evaluated by mixing sufficiently 5 μl of the above-mentioned culture solution, 0.895 ml of the above-mentioned various buffers and 100 mM aqueous p-phenylenediamine in a microcuvette, and then determining for the resulting mixture a change in absorbance at 490 nm with a spectrophotometer (manufactured by Jasco, trade name: V-530).

Figure 3:
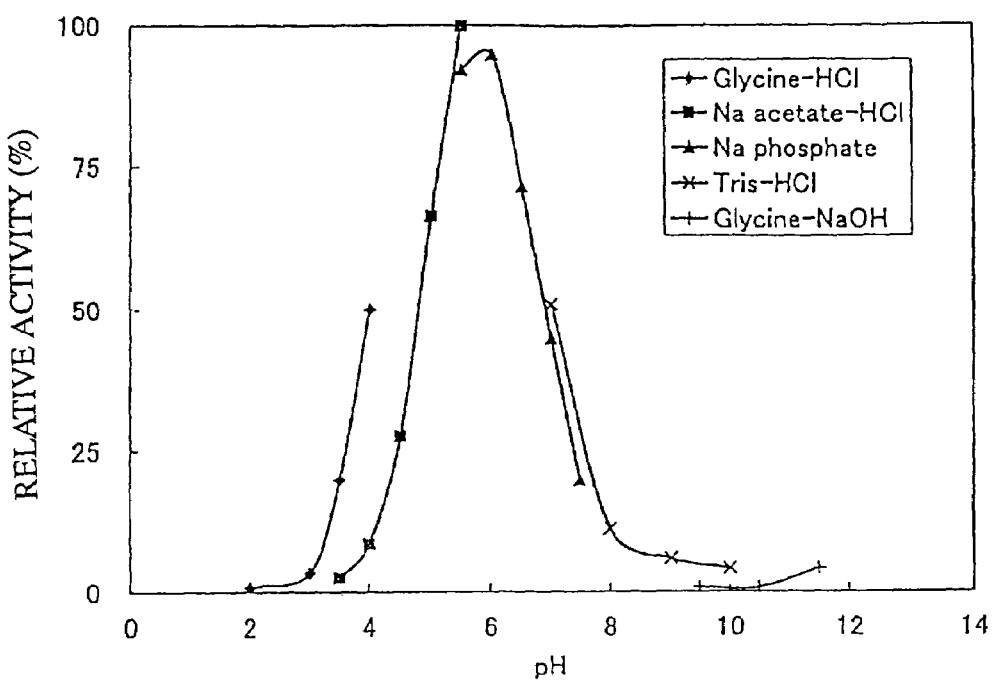
FIG. 3 is a diagram showing the results for examining the optimum pH of the culture of the present invention. Panel A of the figure shows the case where 2,6-dimethoxyphenol was used as a substrate, panel B shows the case where o-aminophenol was used as a substrate, and panel C shows the case where p-phenylenediamine was used as a substrate.
Figure 1:
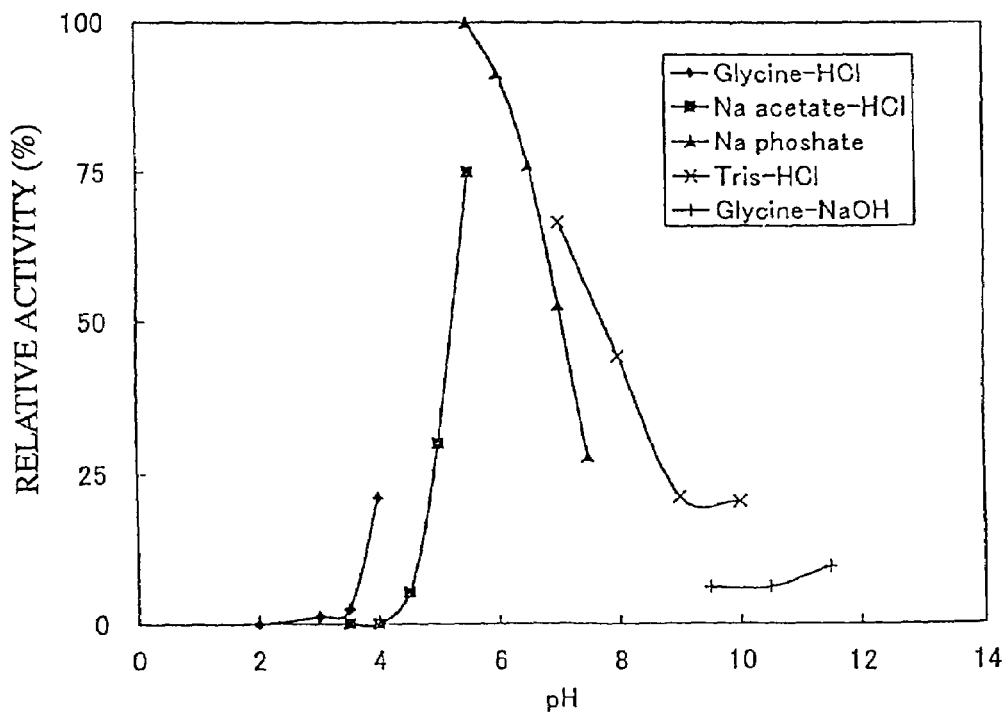
Figures 2, 3:
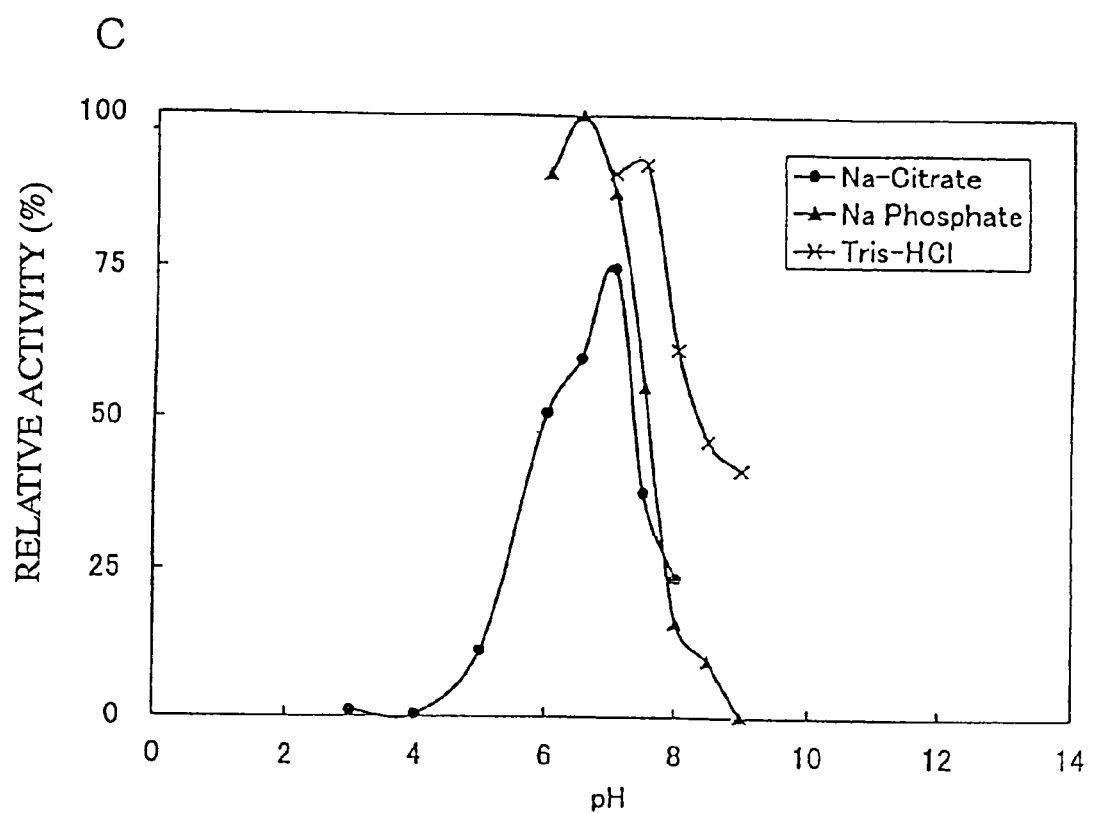

Here, 1 U (unit) of the activity was defined as an amount for increasing the absorbance by 1 per one minute. The results are shown in FIG. 3. In FIG. 3, the activity is expressed as a relative activity, the maximum activity of which is 100. In addition, panel A of the figure shows the case where 2,6-dimethoxyphenol was used as a substrate, panel B shows the case where o-aminophenol was used as a substrate, and panel C shows the case where p-phenylenediamine was used as a substrate.

As shown in FIG. 3, it was found that the optimum pH of the culture of the present invention is about 6.0 when 2,6-dimethoxyphenol is used as a substrate, that the optimum pH is about 6.0 when o-aminophenol is used as a substrate, and that the optimum pH is 6.5 to 8.0 when p-phenylenediamine is used as a substrate.

EXAMPLE 5 pH Stability of Culture of the Present Invention

Pretreatment was carried out by mixing 0.02 ml of the same culture solution as in Example 2 mentioned above with 0.18 ml of one of the various buffers having pHs of from 2 to 11.5, and then incubating the mixture at 30° C. for 1 hour or 20 hours. During the pretreatment, 0.2 M glycine-sodium hydroxide buffer (pH 11.5, pH 10.5, pH 9.5), 0.2 M Tris-HCl buffer (pH 9.0, pH 8.0), 0.2 M sodium phosphate buffer (pH 7.0, pH 6.0), 0.2 M sodium acetate buffer (pH 5.0, pH 4.0) and 0.2 M glycine-HCl buffer (pH 3.0, pH 2.0) were used as buffers depending upon the pHs.

Figure 4:
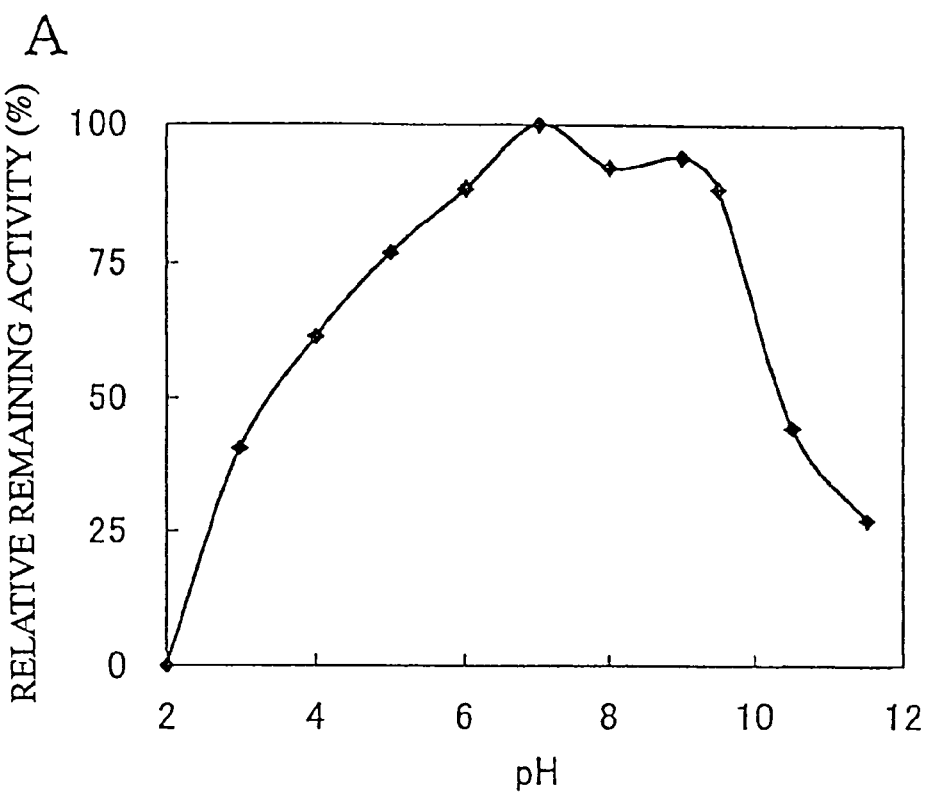
FIG. 4 is a diagram showing the results for examining the pH stability of the culture of the present invention. Panels A and B show the case where 2,6-dimethoxyphenol is used as a substrate, and panels C and D show the case where o-aminophenol is used as a substrate. In addition, panels A and C show the pH stability after 1 hour, and panels B and D show the pH stability after 20 hours.
Figure 1:
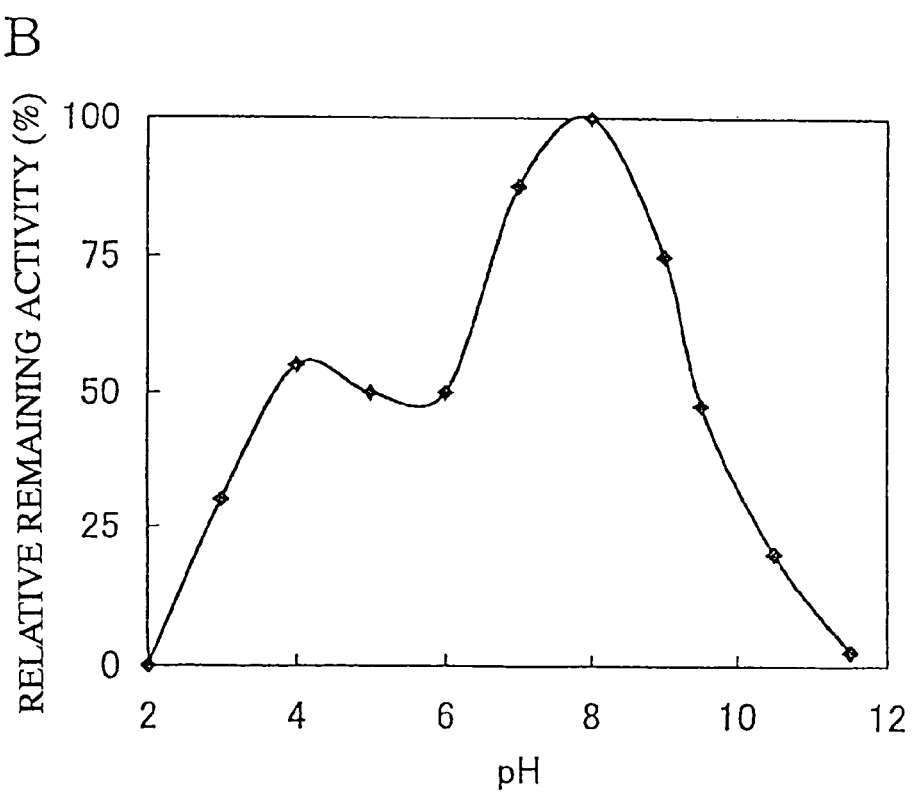
Figure 4:
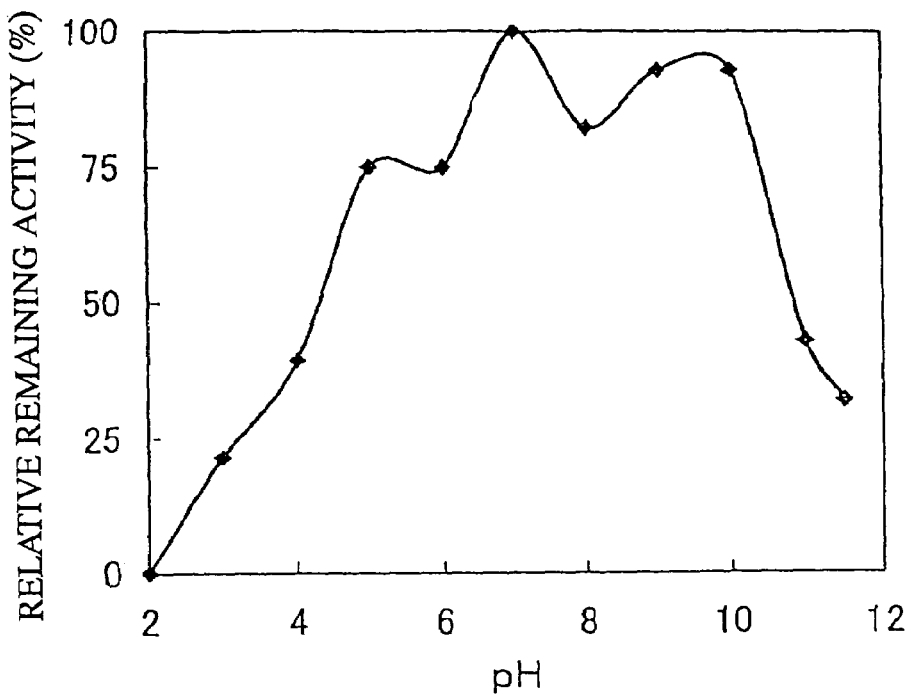
Figure 2:
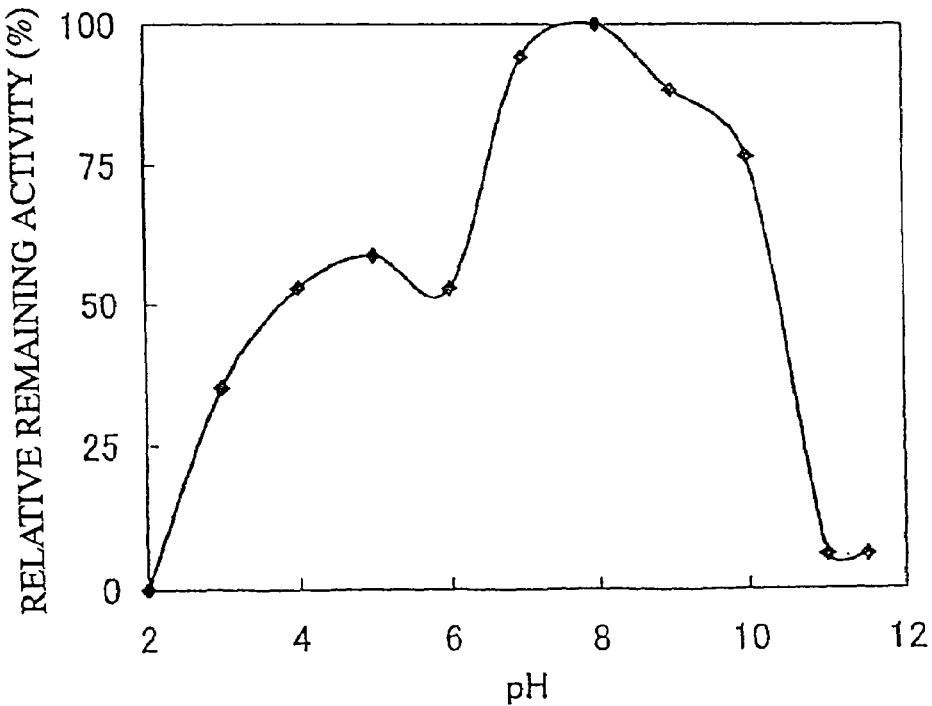

Next, the activity was evaluated by mixing sufficiently 0.02 ml of the culture solution after the pretreatment, 0.88 ml of the above-mentioned buffer, and 0.1 ml of 50 mM o-aminophenol in dimethyl sulfoxide solution in a microcuvette and then determining for the resulting mixture a change in absorbance at 420 nm with a spectrophotometer (manufactured by Jasco, trade name: V-530). Alternatively, when 2,6-dimethoxyphenol was used as a substrate, the same procedures were carried out as in the above-mentioned case where o-aminophenol was used as a substrate by using a 50 mM aqueous 2,6-dimethoxyphenol solution in place of the dimethyl sulfoxide solution of 50 mM o-aminophenol. The activity was evaluated by determining a change in absorbance at 470 nm. Here, 1 U (unit) of the activity was defined as an amount for increasing the absorbance by 1 per one minute. The results are shown in FIG. 4. In FIG. 4, the activity is expressed as a relative remaining activity, the maximum activity of which is 100. In addition, panels A and B show the case where 2,6-dimethoxyphenol is used as a substrate, and panels C and D show the case where o-aminophenol is used as a substrate. Further, panels A and C show the pH stability after 1 hour, and panels B and D show the pH stability after 20 hours.

As shown in FIG. 4, in the case of the 1-hour treatment, the culture of the present invention is stable at pHs of from 6.0 to 10.0 and retains a relative remaining activity of 75%. Also, in the case of the 20-hour treatment, the culture is stable within a pH range of from 7.0 to 9.0 and retains a relative remaining activity of 75%.

EXAMPLE 6

Substrate Specificity of Culture of the Present Invention

In order to examine the substrate specificity of the culture medium, the substrate specificity was examined by using p-phenylenediamine, 4-hydroxyindole, 2-methoxyphenol, 2,6-dimethoxyphenol, catechol, p-aminophenol, o-aminophenol, ABTS, syringaldazine and L-tyrosine were used as substrates. Concretely, the activity was evaluated by mixing sufficiently 0.05 ml of the above-mentioned culture solution, 0.85 ml of 0.1 M sodium phosphate buffer (pH 7.0) with 0.1 ml of a substrate solution (L-tyrosine was used in a concentration of 1.1 mM, syringaldazine was used in a concentration of 1 mM, and others were used in a concentration of 50 mM) in a microcuvette, and determining for the resulting mixture a change in absorbance at 420 nm with a spectrophotometer (manufactured by Jasco, trade name: V-530). Here, 1 U (unit) of the activity was defined as an amount for increasing the absorbance by 1 per one minute. The results are shown in Table 1.

TABLE 1

| Substrate | Determined Wavelength (nm) | U |
|---|---|---|
| p-Phenylenediamine | 470 | 0.101 |
| 4-Hydroxyindole | 470 | 0.078 |
| 2-Methoxyphenol | 470 | 0.117 |
| 2,6-Dimethoxyphenol | 470 | 0.830 |
| Catechol | 400 | 0.029 |
| p-Aminophenol | 400 | 0.072 |
| o-Aminophenol | 420 | 0.262 |
| ABTS | 420 | 0.683 |
| Syringaldazine | 530 | 0.141 |
| L-Tyrosine | 490 | 0.018 |

From the results of Table 1, it was found that the culture of the present invention has phenol oxidase-like activity.

Next, chemical changes of various substrates generated by the action of the culture for the substrate specificity of the culture obtained in (2) of Example 1 was examined by determining a change in the absorbance of the buffer containing each substrate.

As the substrate, commercially available pigments (Evans' Blue, Acid Blue 80, Remazol Brilliant Blue R, Indigo Carmine, Acid Violet 17, Natural Orange) and lignin (trade name: Lignin Alkali, manufactured by Tokyo Kasei) were used. Here, the final concentration and the measuring wavelength for each substrate are shown in Table 2.

TABLE 2

| | Substrate | Final Concentration (g/ml) | Measuring Wavelength (nm) |
|---|---|---|---|
| Azo-Based Pigment | Evans' Blue | 0.007 | 600 |
| Anthraquinone-Based Pigment | Acid Blue 80 | 0.03 | 600 |
| | Remazol Brilliant Blue R | 0.23 | 600 |
| Other Pigments | Indigo Carmine | 0.005 | 600 |
| | Acid Violet 17 | 0.01 | 550 |
| | Natural Orange 6 | 0.03 | 450 |
| Lignin | | 1.00 | 450 |

Concretely, 950 µl of 105.3 mM sodium phosphate buffer (pH 7.0) containing a substrate adjusted to have a final concentration as shown in Table 2 was pre-incubated at 25° C. for 5 minutes. Next, 50 µl of the culture solution was added to the resulting product, and thereafter, the mixture was reacted in a cuvette. The absorbance for each substrate was determined at a measuring wavelength with a spectrophotometer (manufactured by Shimadzu Corporation, trade name: UV-2450). For the comparison, the examination was also made for bilirubin oxidase from a strain belonging to the genus *Myrothecium* in the same manner by replacing the above-mentioned buffer with 105.3 mM Tris-HCl buffer (pH 8.0).

Here, 1 U (unit) of the activity was defined as an amount for increasing the absorbance by 1 per one minute. As to the activity of the culture, the specific activity of each substrate (U/mg protein) is shown in Table 3. In Table 3, a specific activity shown without a sign indicates degradation activity or decolorization activity, and a specific activity shown with—(minus) indicates polymerization activity.

TABLE 3

| | | Specific Activity (U/mg Protein) | |
|---|---|---|---|
| | | | Bilirubin Oxidase from Strain Belonging to Genus *Myrothecium* Reaction pH |
| | Measuring Wavelength | Culture | |
| Substrate | (nm) | 7.0 | 8.0 |
| Azo-Based Pigment | | | |
| Evans' Blue | 600 | 0.32 | 1.22 |
| Anthraquinone-Based Pigment | | | |
| Acid Blue 80 | 600 | 0.30 | 0.39 |
| Remazol Brilliant Blue R | 600 | 0.97 | −0.18 |
| Other Pigments | | | |
| Indigo Carmine | 600 | −0.22 | 0.46 |
| Acid Violet 17 | 550 | 0.12 | −0.40 |
| Natural Orange 6 | 450 | −0.18 | −0.11 |
| Lignin | 450 | 0.73 | −1.63 |

As shown in Table 3, it was found that under neutral conditions, the culture of the present invention catalyzed the oxidative decolorization reaction of the azo-based pigment, the anthraquinone-based pigments and Acid Violet 17; the oxidative degradation reaction of lignin; and the oxidative polymerization reaction of Indigo Carmine and Natural Orange 6. In particular, the culture strongly catalyzed the oxidative decolorization reaction of Remazol Brilliant Blue R and the oxidative degradation reaction of lignin. In addition, the culture of the present invention significantly differs in the specificities for Remazol Brilliant Blue R, Indigo Carmine, Acid Violet 17 and lignin from those of the bilirubin oxidase of a strain belonging to the genus *Myrothecium* used for comparison.

Next, the oxidative coupling reaction of the culture obtained in (2) in Example 1 mentioned above was determined by using color development as an index by the oxidative condensation of the substrate (hydrogen donor) with 4-aminoantipyrine, catalyzed by the culture of the present invention.

As the hydrogen donors, there were used phenolic compounds (phenol, 2-methoxyphenol, 2,6-dimethoxyphenol, catechol, resorcinol, hydroquinone, pyrogallol, gallic acid, propyl gallate, 1-naphthol, catechin), aminophenolic compounds (o-aminophenol, m-aminophenol, p-aminophenol), diaminophenolic compounds (o-phenylenediamine, m-phenylenediamine, p-phenylenediamine), and heterocyclic compounds (5-hydroxyindole, 2,6-diaminopyridine).

The above-mentioned culture solution was added to a reaction system containing 4-aminoantipyrine and an optional hydrogen donor. Thereafter, the activity of the culture of the present invention was assayed by determining a change in absorbance at 490 nm for the phenolic compound, the diaminophenolic compound and the heterocyclic compound, or determining a change in absorbance at 450 nm for the aminophenolic compound. As to a substrate hardly soluble in water, there was used one obtained by dissolving the substrate in a small amount of dimethyl sulfoxide and diluting the resulting solution with deionized water to a desired concentration. The measuring wavelength and the final concentration of each substrate are shown in Table 4. In Table 4, DMSO is an abbreviation for dimethyl sulfoxide.

TABLE 4

| Substrate | Measuring Wavelength (nm) | Final Concentration (mM) |
|---|---|---|
| Phenolic Compounds | | |
| Phenol | 490 | 2.0 |
| 2-Methoxyphenol | 490 | 2.0 |
| 2,6-Dimethoxyphenol | 490 | 2.0 |
| Catechol | 490 | 2.0 |
| Resorcinol | 490 | 2.0 |
| Hydroquinone | 490 | 2.0 |
| Pyrogallol | 490 | 2.0 |
| Gallic acid | 490 | 2.0 |
| Propyl Gallate | 490 | 2.0 (DMSO 1%) |
| 1-Naphthol | 490 | 2.0 (DMSO 1%) |
| Catechin | 490 | 2.0 (DMSO 1%) |
| Aminophenolic Compounds | | |
| o-Aminophenol | 450 | 2.0 (DMSO 1%) |
| m-Aminophenol | 450 | 2.0 (DMSO 1%) |
| p-Aminophenol | 450 | 2.0 (DMSO 1%) |
| Diaminophenolic Compounds | | |
| o-Phenylenediamine | 490 | 2.0 |
| m-Phenylenediamine | 490 | 2.0 |
| p-Phenylenediamine | 490 | 2.0 |
| Heterocyclic Compounds | | |
| 5-Hydroxyindole | 490 | 2.0 (DMSO 1%) |
| 2,6-Diaminopyridine | 490 | 2.0 (DMSO 1%) |

In the table, "%" indicates volume/volume %.

Concretely, 190 μl of 105.3 mM phosphate buffer (pH 7.0) containing 0.4 μmol of a substrate and 4.0 μmol of 4-aminoantipyrine was pre-incubated in wells of a 96-well microplate [manufactured by Corning, Costor (registered trademark) 3368] at 25° C. for 1 minute. Next, 10 μl of the above-mentioned culture solution was added to the resulting mixture, and thereafter, the mixture was incubated for 1 hour. A change in absorbance at 490 nm or 450 nm was determined for the resulting product. One unit (U) of the activity regarding the oxidative coupling reaction was defined as an amount for increasing the absorbance by 1 per one minute.

In addition, for the comparison, the examination was made in the same manner for bilirubin oxidase from the strain of the genus *Myrothecium* except that the above-mentioned buffer was replaced with 105.3 mM Tris-HCl buffer (pH 8.0). The specific activity (U/mg protein) for each substrate is shown in Table 5.

TABLE 5

| | Specific Activity (U/mg Protein) | |
|---|---|---|
| | Culture | Bilirubin Oxidase from Strain Belonging to Genus *Myrothecium* |

| Substrate | Reaction pH 7.0 | Reaction pH 8.0 |
|---|---|---|
| Phenolic Compounds | | |
| Phenol | 8.1 | 0.9 |
| 2-Methoxyphenol | 14.5 | 2.5 |
| 2,6-dimethoxyphenol | 18.1 | 12.0 |
| Catechol | 23.3 | 16.0 |
| Resorcinol | 5.7 | 25.6 |
| Hydroquinone | 2.1 | 0.5 |
| Pyrogallol | 3.2 | −27.6 |
| Gallic acid | 0.9 | 14.9 |
| Propyl Gallate | −0.2 | −0.1 |
| 1-Naphthol | 18.1 | 33.0 |
| Catechin | 14.0 | 4.6 |
| Aminophenolic Compounds | | |
| o-Aminophenol | 22.4 | 15.1 |
| m-Aminophenol | 8.8 | 1.3 |
| p-Aminophenol | 12.7 | 7.0 |
| Diaminophenolic Compounds | | |
| o-Phenylenediamine | 15.1 | 4.5 |
| m-Phenylenediamine | 29.7 | 1.7 |
| p-Phenylenediamine | 20.9 | 11.1 |
| Heterocyclic Compounds | | |
| 5-Hydroxyindole | 4.7 | 1.9 |
| 2,6-Diaminopyridine | 37.7 | 2.3 |

As shown in Table 5, the culture of the present invention catalyzed the oxidative coupling reaction of various phenolic compounds, aminophenolic compounds and diaminophenolic compounds, with the aniline compound 4-aminoantipyrine under neutral conditions (pH 7.0). As to the phenolic compounds, the culture of the present invention was found to have a high activity for the compounds other than gallic acid and propyl gallate. In particular, the culture was found to have an especially high activity for 2-methoxyphenol, 2,6-dimethoxyphenol, catechol, 1-naphthol and catechin. As to the aminophenolic compounds, the culture was found to have a high activity for all of the compounds. In particular, the culture was found to have an especially high activity for o-aminophenol and p-aminophenol. As to the diaminophenolic compounds, the culture was found to have a high activity for all of the compounds. As to the heterocyclic compounds, the culture was found to have a high activity for all of the compounds. In particular, the culture was found to have a high activity for 2,6-diaminopyridine.

In addition, as shown in Table 5, it was found that the culture of the present invention has a substrate specificity significantly different from that of the bilirubin oxidase from the strain belonging to the genus *Myrothecium*, and exhibits a higher specific activity.

Further, the direct oxidation reaction of the culture obtained in the above-mentioned example was determined by using color development due to oxidative polymerization of a substrate generated by the direct action of the culture of the present invention on the substrate as an index.

As the substrates, there were used diaminophenolic compounds (2-chloro 1,4-phenylenediamine, p-phenylenediamine, 2,5-diaminotoluene, N-phenyl-p-phenylenediamine, toluylene-3,4-diamine, m-phenylenediamine), aminophenolic compounds (o-aminophenol, m-aminophenol, 5-amino-o-cresol, p-aminophenol, p-methylaminophenol), and phenolic compounds (2,6-dimethoxyphenol, catechol, resorcinol, hydroquinone, pyrogallol, gallic acid, propyl gallate, 1-naphthol, 1,5-dihydronaphthalene, 2,3,4-trihydroxybenzophenone, 2,3,4,4-tetrahydroxybenzophenone).

As to a substrate hardly soluble in water, there was used one obtained by dissolving the substrate in a small amount of dimethyl sulfoxide and diluting the resulting solution with deionized distilled water to a desired concentration. The measuring wavelength and the final concentration of each substrate are shown in Table 6. In Table 6, %" indicates volume/volume %.

TABLE 6

| Substrate | Measuring Wavelength (nm) | Final Concentration (mM) |
|---|---|---|
| Diaminophenolic Compounds | | |
| 2-Chloro 1,4-phenylenediamine | 490 | 0.50 mM (DMSO 1%) |
| p-Phenylenediamine | 490 | 0.50 mM (DMSO 1%) |
| 2,5-Diaminotoluene | 490 | 0.50 mM (DMSO 1%) |
| N-Phenyl-p-phenylenediamine | 490 | 0.50 mM (DMSO 1%) |
| Toluylene-3,4-diamine | 490 | 0.25 mM (DMSO 1%) |
| m-Phenylenediamine | 405 | 0.50 mM (DMSO 1%) |
| Aminophenolic Compounds | | |
| o-Aminophenol | 450 | 0.50 mM (DMSO 1%) |
| m-Aminophenol | 405 | 0.50 mM (DMSO 1%) |
| 5-Amino-o-cresol | 450 | 0.50 mM (DMSO 1%) |
| p-Aminophenol | 450 | 0.50 mM (DMSO 1%) |
| p-Methylaminophenol | 450 | 0.50 mM (DMSO 1%) |
| Phenolic Compounds | | |
| 2,6-Dimethoxyphenol | 450 | 0.50 mM (DMSO 1%) |
| Catechol | 405 | 0.50 mM (DMSO 1%) |
| Resorcinol | 405 | 0.50 mM (DMSO 1%) |
| Hydroquinone | 405 | 0.50 mM (DMSO 1%) |
| Pyrogallol | 405 | 0.50 mM (DMSO 1%) |
| Gallic Acid | 405 | 0.50 mM (DMSO 1%) |
| Propyl Gallate | 405 | 0.50 mM (DMSO 1%) |
| 1-Naphthol | 405 | 0.50 mM (DMSO 1%) |
| 1,5-Dihydronaphthalene | 405 | 0.50 mM (DMSO 1%) |
| 2,3,4-Trihydroxybenzophenone | 450 | 0.25 mM (DMSO 1%) |
| 2,3,4,4-Tetrahydroxybenzophenone | 450 | 0.25 mM (DMSO 1%) |

Concretely, 180 μl of 0.89 mM sodium phosphate buffer (pH 7.0) containing 0.1 mmol substrate was pre-incubated in wells of a 96-well microplate [manufactured by Corning, Costor (registered trademark) 3368] at 25° C. for 1 minute. Next, 20 μl of the above-mentioned culture solution was added to the resulting mixture. A change in absorbance at 490 nm, 450 nm or 405 nm was determined for the resulting product, depending on the substrate. Here, 1 U (unit) of the activity regarding the direct oxidative reaction was defined as an amount for increasing the absorbance by 1 per one minute.

In addition, for the comparison, the substrate specificities at pH 7.0 for laccase from Japanese lacquer and bilirubin oxidase from the strain belonging to the genus *Myrothecium* were also examined in the same manner.

The relative activity (%) for each substrate is shown in Table 7, in which the measured value for a case where a representative chemical dye 2-chloro 1,4-phenylenediamine was used as a substrate is 100.

TABLE 7

| Substrate | Relative Activity (%) | | |
|---|---|---|---|
| | Culture | Laccase from Japanese Lacquer | Bilirubin Oxidase from Strain Belonging to Genus *Myrothecium* |
| | | Reaction pH | |
| | 7.0 | 7.0 | 7.0 |
| Diaminophenolic Compounds | | | |
| 2-Chloro 1,4-phenylenediamine | 100 | 100 | 100 |
| p-Phenylenediamine | 388 | 142 | 82 |
| 2,5-Diaminotoluene | 80 | 44 | 24 |
| N-Phenyl-p-phenylenediamine | 174 | 94 | 102 |
| Toluylene-3,4-diamine | 120 | 61 | 45 |
| m-Phenylenediamine | 26 | 4 | 14 |
| Aminophenolic Compounds | | | |
| o-Aminophenol | 650 | 103 | 86 |
| m-Aminophenol | 40 | 3 | 3 |
| 5-Amino-o-cresol | 117 | 1 | 19 |
| p-Aminophenol | 235 | 109 | 70 |
| p-Methylaminophenol | 304 | 308 | 122 |
| Phenolic Compounds | | | |
| 2,6-Dimethoxyphenol | 250 | 21 | 69 |
| Catechol | 21 | 2 | 5 |
| Resorcinol | 75 | 25 | 91 |
| Hydroquinone | 20 | 2 | 4 |
| Pyrogallol | 184 | 187 | 104 |
| Gallic Acid | 65 | 9 | 88 |
| Propyl Gallate | 34 | 14 | 85 |
| 1-Naphthol | 17 | 17 | 50 |
| 1,5-Dihydronaphthalene | 63 | 47 | 69 |
| 2,3,4-Trihydroxybenzophenone | 537 | 175 | 62 |
| 2,3,4,4-Tetrahydroxybenzophenone | 571 | 179 | 52 |

As shown in Table 7, the culture of the present invention catalyzed the direct oxidation reaction of various diaminophenolic compounds, aminophenolic compounds and phenolic compounds under neutral conditions (pH 7.0). As to the diaminophenolic compounds, the culture was found to have a high activity for the compounds other than m-phenylenediamine. In particular, the culture was found to have an especially high activity for p-phenylenediamine and N-phenyl-p-phenylenediamine. As to the aminophenolic compounds, the culture was found to have a high activity for the compounds other than m-aminophenol. In particular, the culture was found to have an especially high activity for o-aminophenol, p-aminophenol and p-methylaminophenol. As to the phenolic compounds, the culture was found to have a high activity for 2,6-dimethoxyphenol, pyrogallol, 2,3,4-trihydroxybenzophenone, and 2,3,4,4-tetrahydroxybenzophenone. In particular, the culture was found to have an especially high activity for 2,3,4-trihydroxybenzophenone and 2,3,4,4-tetrahydrobenzophenone.

Also, the culture of the present invention has a higher activity for p-phenylenediamine, m-phenylenediamine, o-aminophenol, m-aminophenol, 5-amino-o-cresol, p-aminophenol, 2,6-dimethoxyphenol, catechol, resorcinol, hydroquinone, gallic acid, propyl gallate, 2,3,4-trihydroxybenzophenone and 2,3,4,4-tetrahydroxybenzophenone, than that of the laccase from Japanese lacquer. In particular, the culture was found to have an even higher activity for m-phenylenediamine, o-aminophenol, m-aminophenol, 5-amino-o-cresol, 2,6-dimethoxyphenol, catechol, hydroquinone and gallic acid.

In addition, the culture of the present invention has a higher activity for p-phenylenediamine, 2,5-diaminotoluene, toluylene-3,4-diamine, o-aminophenol, m-aminophenol, 5-amino-o-cresol, p-aminophenol, p-methylaminophenol, 2,6-dimethoxyphenol, catechol, hydroquinone, propyl gallate, 1-naphthol, 2,3,4-trihydroxybenzophenone and 2,3,4,4-tetrahydroxybenzophenone, than that of the bilirubin oxidase from the strain belonging to the genus *Myrothecium*. In particular, the culture was found to have an even higher activity for o-aminophenol, m-aminophenol, 5-amino-o-cresol, 2,6-dimethoxyphenol, hydroquinone, 1-naphthol, 2,3,4-trihydroxybenzophenone and 2,3,4,4-tetrahydroxybenzophenone.

EXAMPLE 7

Staining with Culture of the Present Invention (1) Stainability with Culture of the Present Invention A staining test was carried out with the culture obtained in Example 1 mentioned above. A yak hair bundle and a wool cloth were stained with dyes (p-phenylenediamine and o-aminophenol) with the above-mentioned culture by oxidative polymerization. Concretely, 0.5 g of a dye (or 1.0 g in total when the 2 kinds of dyes were used), 0.75 g of hydroxyethyl cellulose (HEC) as a thickener, 1.0 g of polyoxyethylene(20) hydrogenated castor oil (HC-20) as a surfactant, and 0.5 g of lactic acid were mixed, and the pH was adjusted to 7.0 with monoethanolamine. Deionized water was added to the mixture to make up a weight of 50 g, to give a base material.

Two grams of the above-mentioned base material and the above-mentioned culture solution (amount equivalent to 3.5 U) were mixed, and the mixture obtained was applied to each of 1 g of yak hair bundle and one piece of a wool cloth (2×3 cm). Each of the yak hair bundle and the wool cloth after the application was kept at 30° C. for 1 hour. The activity in the above-mentioned culture solution is an activity determined using 30 mM p-phenylenediamine as the substrate under the conditions of pH 7.0 and 25° C.

L value, a value and b value for the stained yak hair bundle and the wool cloth were determined with a colorimeter (manufactured by Minolta, trade name: Chromometer CM-3610d). Next, on the bases of the above-mentioned L value, a value and b value, $\Delta E$ value was calculated from the equation 1:

$$\Delta E = \sqrt{(\Delta L)^2 + (\Delta a)^2 + (\Delta b)^2}$$

The stainability of the culture was evaluated from the above $\Delta E$ value. The $\Delta E$ value indicates a difference between the color tone of the yak hair bundle and the wool cloth before staining and the color tone of the yak hair bundle and the wool cloth after staining. For the comparison, a staining test was carried out in the same manner as the laccase from Japanese lacquer. The $\Delta E$ value for each substrate is shown in Table 8.

TABLE 8

| | | ΔE | |
|---|---|---|---|
| | | Yak Hair Bundle | Wool Cloth |
| p-Phenylenediamine | Without Enzyme | 9.39 | 8.02 |
| | Laccase from | 43.66 | 49.58 |
| | Japanese Lacquer | (34.27) | (41.56) |
| | Culture | 42.22 | 44.53 |
| | | (32.83) | (36.51) |
| o-Aminophenol | Without Enzyme | 16.84 | 14.74 |
| | Laccase from | 43.91 | 38.27 |
| | Japanese Lacquer | (27.07) | (23.53) |
| | Culture | 45.63 | 48.20 |
| | | (28.79) | (33.46) |
| o-Aminophenol + p-Phenylenediamine | Without Enzyme | 20.23 | 14.01 |
| | Laccase from | 33.26 | 41.35 |
| | Japanese Lacquer | (13.03) | (27.34) |
| | Culture | 33.23 | 39.17 |
| | | (13.00) | (25.16) |
| o-Aminophenol + m-Phenylenediamine | Without Enzyme | 20.52 | 10.59 |
| | Laccase from | 32.66 | 26.30 |
| | Japanese Lacquer | (12.14) | (15.71) |
| | Culture | 38.38 | 45.54 |
| | | (17.86) | (34.95) |

As shown in Table 8, according to the culture of the present invention, evident stainability was recognized for the yak hair bundle and the wool cloth in any combinations of dyes. Also, according to the culture of the present invention, it was found that although the stainability with p-phenylenediamine alone or with o-aminophenol+p-phenylenediamine was slightly inferior, the stainability with o-aminophenol alone and with o-aminophenol+m-phenylenediamine was evidently superior, than that of the laccase from Japanese lacquer used for comparison.

(2) Studies on Amount Used of Culture of the Present Invention

A staining test was carried out with the culture of the present invention with varying amounts of the culture obtained in Example 1 mentioned above. Using a dye (o-aminophenol) which is to be oxidized with the culture of the present invention, the yak hair bundle and the wool cloth were stained by oxidative polymerization, and L value, a value and b value were determined by a calorimeter.

Concretely, 0.5 g of o-aminophenol as a dye (substrate), 0.5 g of m-phenylenediamine as a coupler, 0.75 g of hydroxyethyl cellulose (HEC) as a thickener, 1.0 g of polyoxyethylene(20) castor oil (HC-20) as a surfactant, and 0.5 g of lactic acid were mixed, and the pH of the mixture was adjusted to 7.0 with monoethanolamine. Deionized water was added to the mixture to make up a weight of 50 g, to give a base material.

In addition, for 1 g of the yak hair bundle and 1 piece of the wool cloth (2×3 cm), 2 g of the above-mentioned base material and a culture solution adjusted so as to contain 0 to 0.8 mg as an amount of protein in the culture. The resulting mixture was applied to 1 g of the yak hair bundle and 1 piece of the wool cloth (2×3 cm). Each of the yak hair bundle and the wool cloth after the application was kept at 30° C. for 1 hour.

Figure 5:
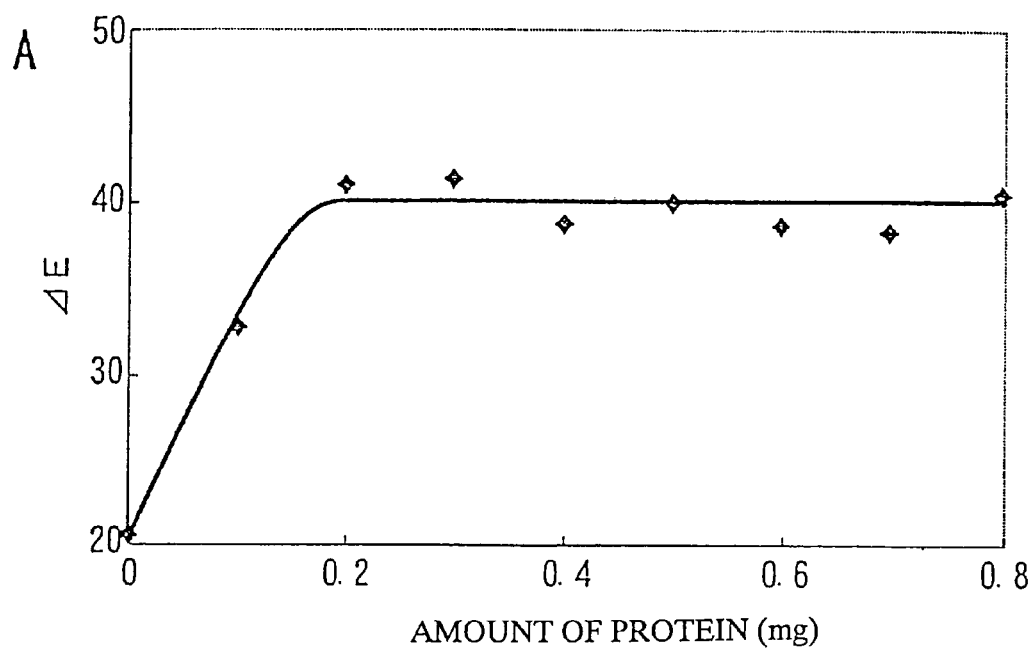
FIG. 5 is a diagram showing the results for staining the yak hair bundle and the wool cloth with the culture of the present invention.
Figure 5:
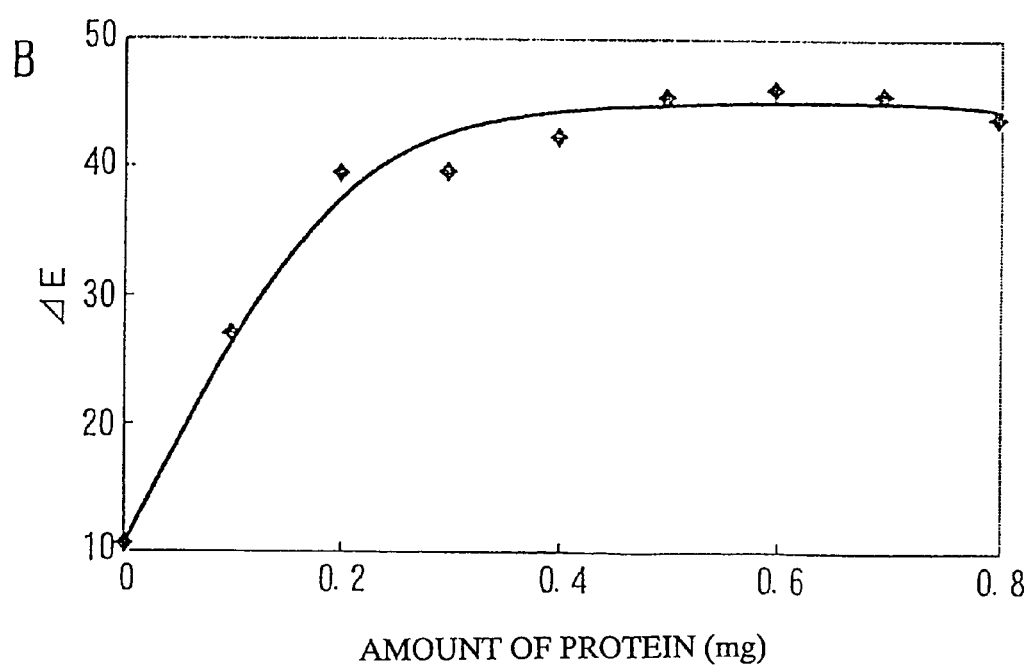

L value, a value and b value were determined for the stained yak hair bundle and the wool cloth with a colorimeter (manufactured by Minolta, trade name: Chromometer CM-3610d), and ΔE value was calculated therefrom. The stainability of the culture was evaluated by the ΔE value. A change in ΔE value according to the amount of the culture of the present invention used is shown in FIG. 5. Panel A of FIG. 5 shows the results using the yak hair bundle, and panel B shows the results using the wool cloth.

As shown in FIG. 5, in the yak hair bundle and the wool cloth, the ΔE value increased by increasing the amount of the culture of the present invention used. The ΔE value in the yak hair bundle reached a given value by the culture of the present invention in an amount equivalent to 0.2 mg protein, while the ΔE value in the wool cloth reached a given value by the culture of the present invention in an amount equivalent to 0.5 mg protein.

EXAMPLE 8

Studies on Conditions for Inducing Phenol Oxidase-Like Activity (1) Culture of Fungal Cells The culture (liquid culture) obtained in (1) in Example 1 mentioned above was cultured in the liquid culture medium 2 (medium described in Example 1) under five culture pH conditions within the range of weakly acidic to weakly alkaline (initial pH: pH 5.0, pH 6.0, pH 7.0, pH 8.0, pH 9.0), and a difference in the oxidative activity (induction of phenol oxidase-like activity) was examined.

The above-mentioned liquid culture was stirred well, and thereafter, 0.5 ml of the resulting culture was added to 100 ml of a medium for inducing the activity. The resulting mixture was cultured with shaking (shaking rate 130 rotations/minute) in a thermostatic bath at 28° C. for 10 days.

The culture was collected 1 mg every day and centrifuged at 12000 rpm at 4° C. for 5 minutes. Supernatant was filtered with DISMIC-25cs (0.20 μm) to remove the Fungal Cells.

The sample obtained was preserved at 4° C.

(2) Studies on Change in Induction of Activity According to Culture pH Conditions The change in induction of the activity according to culture pH conditions was examined by assaying the phenol oxidase-like activity of each sample obtained in the above-mentioned (1).

In the assay of the phenol oxidase-like activity, the phenol oxidase-like activity was assayed under the reaction pH condition of pH 6.0 by using 2,6-dimethoxyphenol as a substrate.

To a semimicrocuvette were added 0.20 ml of 500 mM sodium phosphate buffer (pH 6.0), 0.65 ml of deionized distilled water, 0.10 ml of 50 mM substrate solution mentioned above and 0.05 ml of the culture, with stirring. The change in absorbance at 470 nm from 0 to 30 seconds at room temperature was determined with trade name: UV-2400 (manufactured by Shimadzu Corporation). The change in induction of the activity according to the culture pH conditions is shown in FIG. 6.

Figure 6:
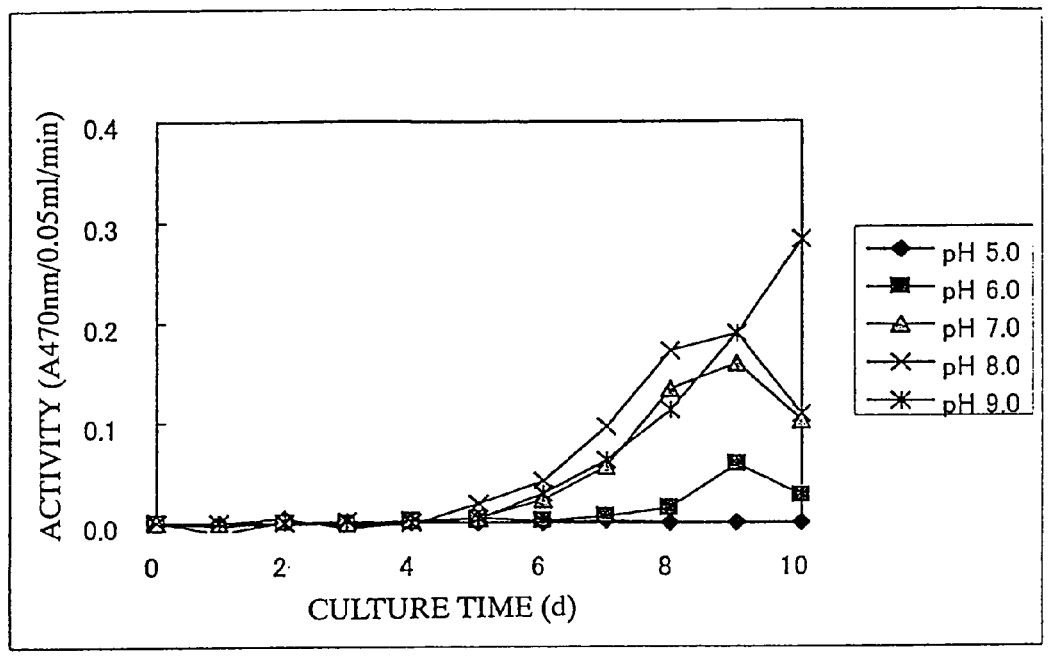
FIG. 6 is a diagram showing the results for examining the change in the induction of the activity depending upon the culture pH conditions.

As a result, as shown in FIG. 6, it is found that the higher the pH of the medium used is, the higher the enzyme activity at a pH of 6.0, which is the reaction optimum pH for 2,6-dimethoxyphenol. Especially, when the pH of the medium used is a value exceeding a pH of 7.0 (pH of about 7.3 during the culture), it is found that the enzyme activity at a pH of 6.0, which is the reaction optimum pH for 2,6-dimethoxyphenol, becomes high.

On the other hand, when the pH of the medium used is a pH of 5.0, the enzyme activity for 2,6-dimethoxyphenol was not recognized even when the bacterial cells were cultured for 10 days.

In addition, as shown in FIG. 6, when the pH of the medium used is a pH of 9.0, it is seen that the activity on the tenth day of the culture is about 10 times (0.283/0.027) higher than the activity on the tenth day of the culture when the pH of the medium used is a pH of 6.0.

Therefore, it is found that the phenol oxidase-like activity in the culture is more induced by using the medium having a pH value of higher than 7.0.

TEST EXAMPLE (1) Culture of Fungal Cells

Two-hundred-and-fifty grams of soybeans were disrupted with a mixer, the disruption obtained was placed in a 1-L eggplant-shape flask, and 750 ml of hexane was added thereto. The resulting mixture was stirred with a glass rod until the hexane turned pale yellow, and thereafter the mixture was heated at 85° C. in an oil bath. One hour after the beginning of heating, the heating was terminated, and thereafter, the resulting product was filtered with No. 2 filter paper manufactured by ADVANTEC.

Thereafter, the resulting filtrate was further subjected to suction filtration. The filtrate was allowed to stand in a draft for 24 hours to evaporate the hexane, thereby drying the resulting soybean dregs.

Next, a medium (composition: 2.0% by weight glucose, 1.0% by weight sucrose, 2.0% by weight soybean dregs, 0.5% by weight corn steep liquor, 0.1% by weight $K_2HPO_4$, 0.05% by weight $MgSO_4 \cdot 7H_2O$, 10 γ/ml, $FeCl_2 \cdot 6H_2O$, pH 6.0) was prepared. The medium is a medium described in Japanese Patent Laid-Open No. Sho 60-156385.

To a 300-ml Erlenmeyer flask containing 30 ml of the above-mentioned medium was added 0.2 ml of the culture (liquid medium) obtained in (1) in Example 1 mentioned above. The mixture was cultured with shaking (shaking rate: 130 rotations/min.) in a thermostatic bath at 28° C. for 4 days. Next, the resulting culture medium was added to a 2-L Erlenmeyer flask containing 300 ml of the above-mentioned medium, and thereafter, the mixture was cultured with shaking (shaking rate: 130 rotations/min.) for 4 days under room-temperature conditions of 20° to 25° C.

After the termination of culture, the culture medium was subjected to suction filtration through No. 2 filter paper manufactured by ADVANTEC to remove the cells. Thereafter, the resulting filtrate was centrifuged at 4° C. at 14,800 rpm (30,000×g) for 30 minutes, to give a supernatant as the culture. The resulting culture was preserved at 4° C.

(2) Change in Enzyme Activity According to Reaction pH Conditions

In the assay of the phenol oxidase-like activity, each of 2,6-dimethoxyphenol and p-phenylenediamine was used as a substrate. Also, in the assay of the phenol oxidase-like activity, there were used glycine-HCl buffer at a pH of 2.5 to 4.0, sodium acetate buffer at a pH of 4.0 to 5.5, sodium phosphate buffer at a pH of 5.5 to 7.5, Tris-HCl buffer at a pH of 7.5 to 8.5 and glycine-NaOH buffer at a pH of 8.5 to 11.0. Incidentally, when p-phenylenediamine is used as a substrate, in the assay of the phenol oxidase-like activity, the assay was also carried out using sodium citrate buffer at a pH of 3.0 to 7.0.

Figure 7:
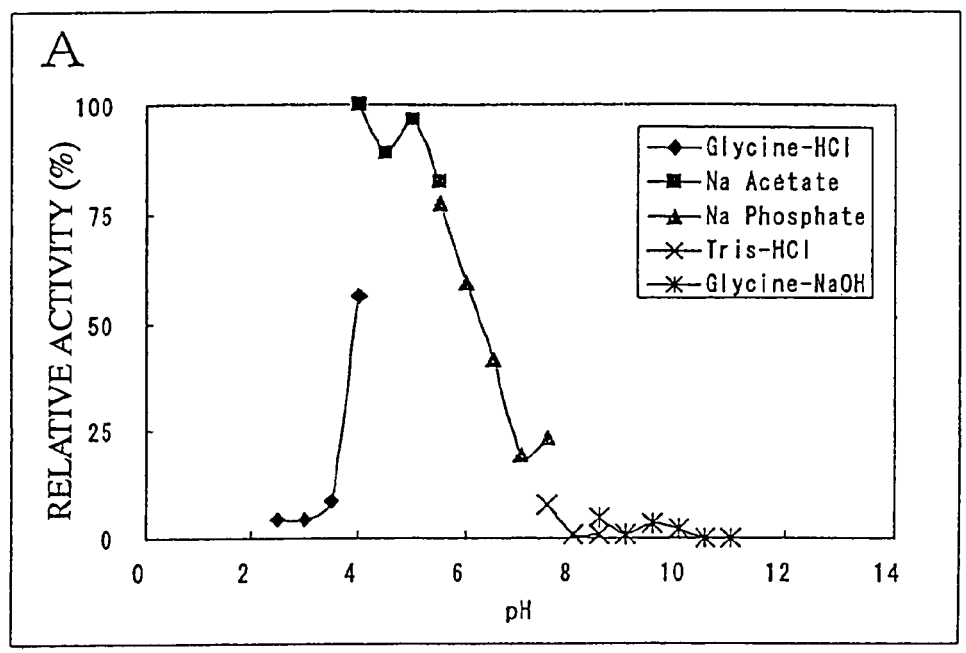
FIG. 7 is a diagram showing the results comparing the optimum pH of the phenol oxidase-like activity of each of the culture of the present invention and the culture obtained by culturing at a pH of 6.0. Panels A and B show optimum pH of the culture obtained by culturing at a pH of 6.0, and panels C and D show optimum pH of the culture of the present invention. In addition, panels A and C show cases where 2,6-dimethoxyphenol is used as a substrate, and panels B and D show cases where p-phenylenediamine is used as a substrate.
Figure 1:
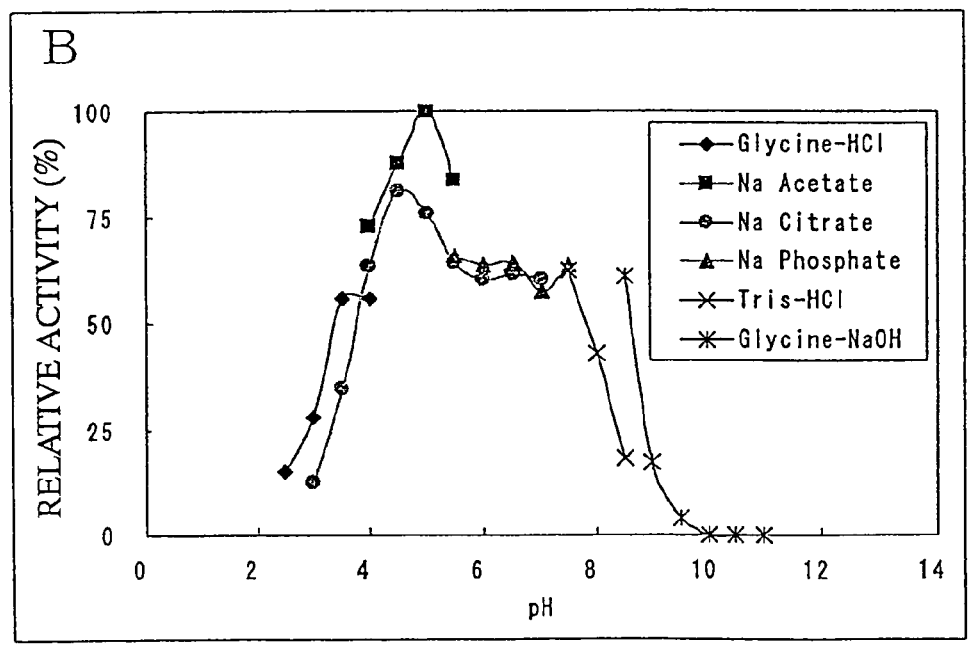
Figure 7:
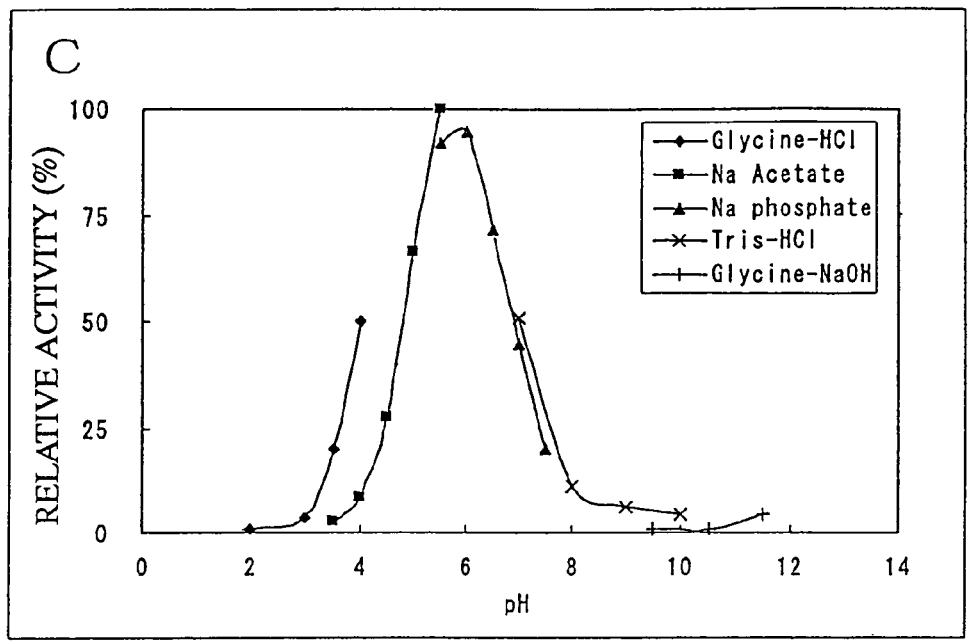
Figure 2:
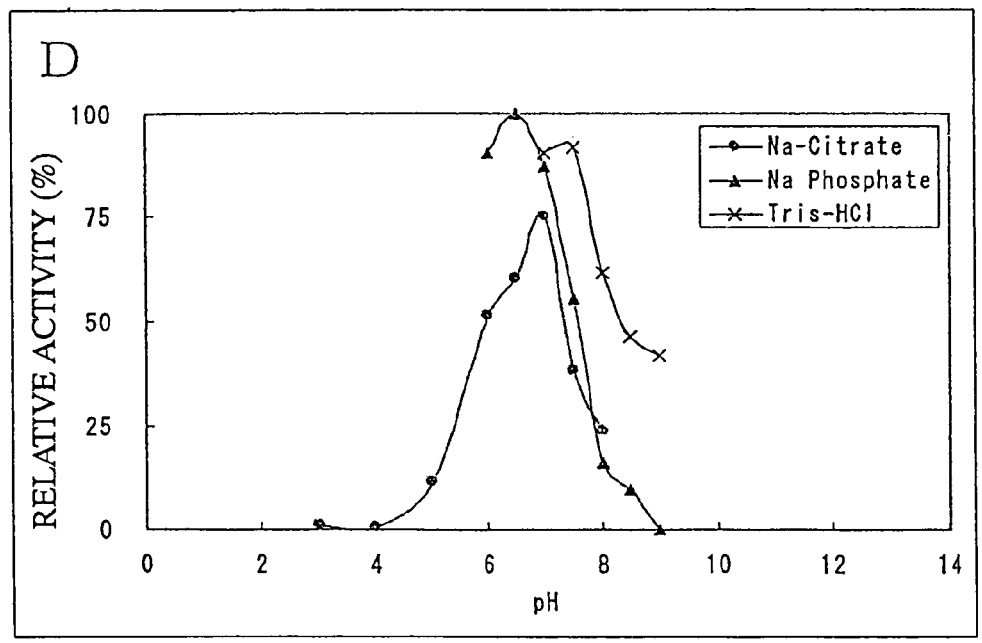

To a semimicrocuvette were added 0.20 ml of a 500 mM buffer mentioned above, 0.65 ml of deionized distilled water, 0.10 ml of a 50 mM substrate solution mentioned above, and 0.05 ml of the culture with stirring. The change in absorbance at 470 nm from 0 to 30 seconds was determined at room temperature with trade name: UV-2400 (manufactured by Shimadzu Corporation). Incidentally, the phenol oxidase-like activity was also assayed in the same manner for the culture of the present invention obtained in Example 1 mentioned above. These results are shown in FIG. 7.

As a result, it was shown that the case of the culture (panels A and B in FIG. 7) obtained in the above (1) has an optimum pH on an acidic pH as compared to the case of the culture of the present invention (panels C and D in FIG. 7) obtained in Example 1 even when using any of the substrates.

Therefore, it is found that the phenol oxidase-like activity of the culture of the present invention and the phenol oxidase-like activity of the culture obtained by culturing under the condition of a pH of 6.0. are evidently different from each other.

FORMULATION EXAMPLES

Formulation Examples of the staining composition according to the present invention will be shown hereinbelow. When the following composition is applied to white hair, the white hair can be stained to obscure the white hair. Here, the amounts blended are expressed in % by weight.

| Formulation Example 1 (Gel Type) | |
|---|---|
| p-Phenylenediamine | 1.5 |
| Resorcin | 0.3 |
| m-Metaaminophenol | 0.1 |
| Culture of (2) of Example 1 | 0.1 |
| Sodium Ascorbate | 1.0 |
| Hydroxyethyl Cellulose | 1.0 |
| Citric Acid | Proper Amount |
| Monoethanolamine | Adjusted to pH of 7 |
| Purified Water | Balance |
| Total | 100.0 |
| Formulation Example 2 (Cream Type) | |
| p-Phenylenediamine | 1.0 |
| p-Aminophenol | 0.8 |
| m-Aminophenol | 0.1 |
| Cetanol | 6.0 |
| Culture of (2) of Example 1 | 0.05 |
| Polyoxyethylene(20) Cetyl Ether | 4.0 |
| Stearyltrimethylammonium Chloride | 1.0 |
| L-Cysteine Hydrochloride | 0.2 |
| Citric Acid | Proper Amount |
| Monoethanolamine | Adjusted to pH of 7 |
| Purified Water | Balance |
| Total | 100.0 |
| Formulation Example 3 (Cream Type) | |
| 5,6-Dihydroxyindoline | 1.0 |
| 5,6-Dihydroxyindole-2-carboxylic Acid | 0.5 |
| o-Aminophenol | 0.5 |
| Ethanol | 5.0 |
| Stearyl Alcohol | 1.5 |
| Culture of (2) of Example 1 | 0.2 |
| Polyoxyethylene(40) Hydrogenated Castor Oil | 3.0 |
| Polyglycerol Fatty Acid Ester | 4.0 |
| N-Acetylcysteine | 0.1 |
| Xanthane gum | 0.5 |
| ACCULIN (Registered Trademark) 22 | 0.1 |
| Hydroxyethyl Cellulose | 0.1 |
| Monoisopropanolamine | Proper Amount |
| Monoethanolamine | Proper Amount |
| Purified Water | Balance |
| Total | 100.0 |

-continued

| Formulation Example 4 (Aerosol Type) | |
|---|---|
| Toluene-2,5-diamine | 1.5 |
| p-Aminophenol | 0.2 |
| Resorcin | 0.1 |
| m-Aminophenol | 0.1 |
| Polyoxyethylene (15) Cetyl Ether | 2.0 |
| Propylene Glycol | 5.0 |
| Sodium Sulfite | 0.3 |
| Monoethanolamine | Proper Amount |
| Citric Acid | Proper Amount |
| Culture of (2) of Example 1 | 0.3 |
| Liquefied Petroleum Gas | 4.0 |
| Purified Water | Balance |
| Total | 100.0 |

INDUSTRIAL APPLICABILITY

According to the culture of the present invention, there can be utilized in staining of fiber and hair, bleaching of pulp and fiber, removal of a phenolic compound in waste liquor, degradation of endocrine disruptors, preparation of a phenol resin, production of artificial Japanese lacquer, improvement in woody properties and the like, which can be carried out inexpensively and conveniently. In addition, according to the method for producing the culture according to the present invention, the above-mentioned culture can be obtained conveniently, inexpensively and in a large amount. Further, according to the staining method and the staining composition of the present invention, a subject to be stained can be stained efficiently at a nearly neutral pH, inexpensively and conveniently, with any of various dyes, especially phenolic compounds, aminophenolic compounds, and phenylenediamine compounds without significant fluctuation in the optimum pH under external environmental conditions. Therefore, the staining method and the staining composition are useful in staining of fiber and hair.

The invention claimed is:

1. A culture from a strain belonging to the genus *Flammulina*, wherein the culture has phenol oxidase-like activity and at least one substrate specificity selected from the group consisting of ① to ⑤:

① catalyzing an oxidative decolorization reaction [decolorization activity] of each of:

Evans' Blue represented by the formula (I):

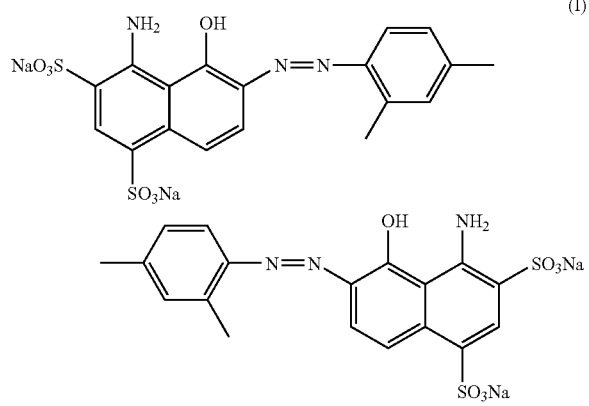

Acid Blue 80 represented by the formula (II):

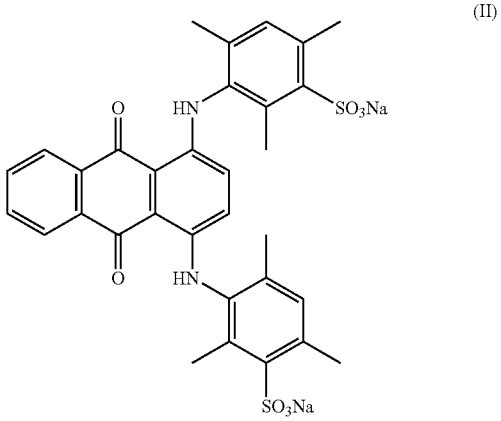

Remazol Brilliant Blue R represented by the formula (III):

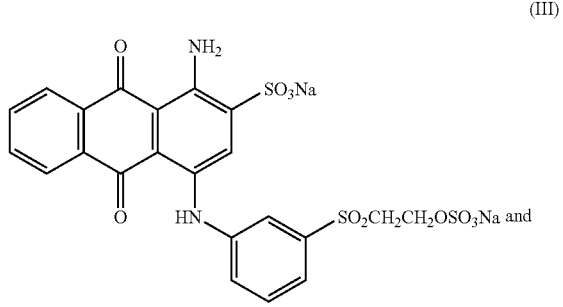

Acid Violet 17 represented by the formula (IV):

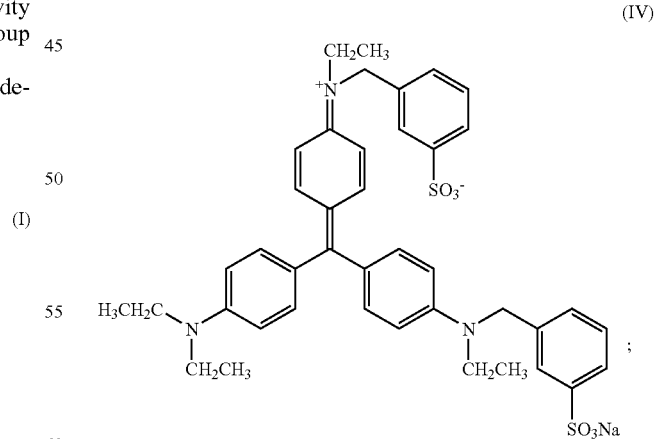

② catalyzing oxidative degradation reaction [oxidative degradation activity] for lignin;

③ catalyzing oxidative polymerization reaction [oxidative polymerization activity] of Indigo Carmine represented by the formula (V):

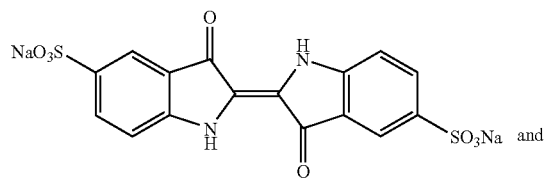

Natural Orange 6 represented by the formula (VI):

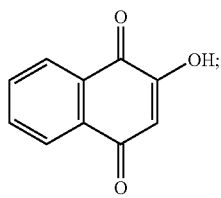

④ catalyzing oxidative coupling reaction [oxidative coupling activity] of 4-aminoantipyrine with one kind of a compound selected from the group consisting of phenolic compounds, aminophenolic compounds, diaminophenolic compounds and heterocyclic compounds; and ⑤ catalyzing direct oxidative reaction [direct oxidation activity] of one kind of a compound selected from the group consisting of phenolic compounds, aminophenolic compounds, diaminophenolic compounds and heterocyclic compounds, wherein the culture is obtainable by culturing a strain belonging to the genus *Flammulina* under pH conditions exceeding a pH of 7, and removing hyphae from the resulting culture medium.

2. The culture according to claim 1, wherein the strain belonging to the genus *Flammulina* is *Flammulina velutipes*.

3. The culture according to claim 2, wherein *Flammulina velutipes* is *Flammulina velutipes* strain IFO 30601.

4. A culture from a strain belonging to the genus *Flammulina*, wherein the culture is obtainable by culturing a strain belonging to the genus *Flammulina* under pH conditions exceeding a pH of 7, and removing hyphae from the resulting culture medium, wherein the culture has phenol oxidase-like activity.

5. A method for producing the culture from a strain belonging to the genus *Flammulina* according to claim 1, characterized in that the method comprises culturing a strain belonging to the genus *Flammulina* under pH conditions exceeding a pH of 7, and removing hyphae from the resulting culture medium, to give a culture.

6. The method according to claim 5, wherein the strain belonging to the genus *Flammulina* is *Flammulina velutipes*.

7. The method according to claim 6, wherein *Flammulina velutipes* is *Flammulina velutipes* strain IFO 30601.

8. A staining method characterized in that the staining method comprises contacting a subject to be stained with a dye in the presence of the culture of claim 1.

9. A staining composition comprising the culture of claim 1.

* * * * *